(12) United States Patent
Dasgupta et al.

(10) Patent No.: US 9,759,668 B2
(45) Date of Patent: Sep. 12, 2017

(54) SYSTEMS AND METHODS FOR LIQUID QUALITY ASSESSMENT

(71) Applicant: UNIVERSITY OF CALCUTTA, Kolkata (IN)

(72) Inventors: Anjan Kr. Dasgupta, Kolkata (IN); Sufi Oasim Raja, Kolkata (IN)

(73) Assignee: UNIVERSITY OF CALCUTTA, Kolkata (IN)

( * ) Notice: Subject to any disclaimer, the term of this patent is extended or adjusted under 35 U.S.C. 154(b) by 0 days.

(21) Appl. No.: 14/910,809

(22) PCT Filed: Aug. 8, 2014

(86) PCT No.: PCT/IB2014/063798
§ 371 (c)(1),
(2) Date: Feb. 8, 2016

(87) PCT Pub. No.: WO2015/019327
PCT Pub. Date: Feb. 12, 2015

(65) Prior Publication Data
US 2016/0195478 A1    Jul. 7, 2016

(30) Foreign Application Priority Data
Aug. 9, 2013  (IN) .............................. 943/KOL/2013

(51) Int. Cl.
*G01N 21/00* (2006.01)
*G01N 21/94* (2006.01)
(Continued)

(52) U.S. Cl.
CPC ............. *G01N 21/94* (2013.01); *G01N 21/49* (2013.01); *G01N 21/82* (2013.01); *G01N 33/1813* (2013.01); *G01N 2201/0683* (2013.01)

(58) Field of Classification Search
CPC ........... G01N 21/31; G01N 2021/3181; G01N 21/274; G01N 21/65; G01N 2021/3148;
(Continued)

(56) References Cited

U.S. PATENT DOCUMENTS 5,550,053 A  *  8/1996  Salpeter ............... G01N 21/274
                                                   250/252.1
5,599,717 A  *  2/1997  Vo-Dinh ............... A61B 5/0059
                                                   436/171

(Continued)

FOREIGN PATENT DOCUMENTS

JP       2009236831 A      10/2009

OTHER PUBLICATIONS

Alexander, G.B., "The Reaction of Low Molecular Weight Silicic Acids with Molybdic Acid," Journal of the American Chemical Society, vol. 75, Issue 22, pp. 5655-5657 (Nov. 1953).
(Continued)

*Primary Examiner* — Michael P Stafira
(74) *Attorney, Agent, or Firm* — Maschoff Brennan

(57) ABSTRACT

The present technology provides liquid quality assessment systems and methods for their preparation and use. The systems can include a light source configured to illuminate a liquid sample, a reflecting surface configured to reflect light scattered by the liquid sample, and a detector configured to detect light intensity, wherein the light source illuminates the liquid sample with a first incident light when the reflecting surface is absent; the detector detects a first light scattered by the liquid sample in response to the first incident light; the light source illuminates the liquid sample with a second incident light when the reflecting surface is present; and the detector detects a second light which is a combination of light scattered by the liquid sample in response to the second incident light and light reflected by
(Continued)

the reflecting surface of light scattered by the liquid sample in response to the second incident light.

20 Claims, 17 Drawing Sheets

(51) Int. Cl.
*G01N 21/49* (2006.01)
*G01N 21/82* (2006.01)
*G01N 33/18* (2006.01)

(58) Field of Classification Search
CPC ......... G01N 2021/8514; G01N 21/314; G01N 21/3151; G01N 21/35; G01N 21/3504; G01N 21/3577; G01N 21/8507; G01N 21/94
See application file for complete search history.

(56) References Cited

U.S. PATENT DOCUMENTS

| | | | | |
|---|---|---|---|---|
| 5,710,630 | A * | 1/1998 | Essenpreis | A61B 5/14532 250/227.27 |
| 6,040,906 | A * | 3/2000 | Harhay | G01N 21/65 356/301 |
| 6,636,308 | B1 * | 10/2003 | Tsutsui | G01N 21/474 356/336 |
| 2003/0025877 | A1 * | 2/2003 | Yancey | A61B 3/152 351/221 |
| 2005/0095601 | A1 * | 5/2005 | Cullum | G01N 21/6428 435/6.11 |
| 2005/0288564 | A1 * | 12/2005 | Iuliano | A61B 5/14532 600/318 |
| 2007/0117215 | A1 * | 5/2007 | Davis | G01N 21/643 436/172 |
| 2007/0222988 | A1 * | 9/2007 | Jiang | G01J 3/02 356/367 |
| 2009/0218499 | A1 * | 9/2009 | Kimura | G01N 21/648 250/363.01 |
| 2010/0120132 | A1 * | 5/2010 | Koo | G01N 33/54346 435/287.2 |
| 2010/0315639 | A1 * | 12/2010 | Muraki | G01N 15/1484 356/342 |
| 2012/0002960 | A1 * | 1/2012 | Laitinen | G01N 21/6452 398/25 |
| 2012/0267551 | A1 * | 10/2012 | Dasgupta | G01N 21/6445 250/453.11 |
| 2012/0287435 | A1 | 11/2012 | Adams et al. | |
| 2013/0169963 | A1 * | 7/2013 | Junnarkar | G01N 21/53 356/343 |

OTHER PUBLICATIONS

Barron, L.D., and Buckingham., A.D., "Rayleigh and Raman scattering by molecules in magnetic fields," Molecular Physics: An International Journal at the Interface between Chemistry and Physics, vol. 23, Issue 1, pp. 145-150 (1972).

Aleksandrov, V.D., et al., "Effect of Magnetic Field on the Supercooling of Water Drops," Inorganic materials, vol. 36, Issue 9 pp. 895-898 (Sep. 2000).

Amiri, M.C., and Dadkhah, A. A., "On reduction in the surface tension of water due to magnetic treatment," Colloids and Surfaces A: Physicochemical and Engineering Aspects, vol. 278, Issue 1-3, pp. 252-255 (Apr. 20, 2006).

Chang, K-T., and Weng, C-I., "The effect of an external magnetic field on the structure of liquid water using molecular dynamics simulation," Journal of Applied Physics, vol. 100, Issue 4, pp. 043917-1-043917-6 (2006).

Cho, Y-I., and Lee, S-H., "Reduction in the surface tension of water due to physical water treatment for fouling control in heat exchangers," International Communications in Heat and Mass Transfer, vol. 32, Issue 1-2, pp. 1-9 (Jan. 2005).

Collings, P. J., et al., "Resonance Light Scattering and Its Application in Determining the Size, Shape, and Aggregation Number for Supramolecular Assemblies of Chromophores," The Journal of Physical Chemistry B, vol. 103, Issue 40, pp. 8474-8481 (1999).

Hasson, D., and Bramson, D., "Effectiveness of magnetic water treatment in suppressing calcium carbonate scale deposition," Industrial & Engineering Chemistry Process Design and Development, vol. 24, Issue 3, pp. 588-592 (Jul. 1985).

International Search Report and Written Opinion for International Application No. PCT/IB2014/063798 mailed Dec. 31, 2014.

Jiang, Z-L., et al., "A new immune resonance scattering spectral assay for trace fibrinogen with gold nanoparticle label," Analytica Chimica Acta, vol. 571, Issue 2, pp. 200-205 (Jul. 7, 2006).

Meyers, P., "Behavior of Silica in Ion Exchange and Other Systems," IWC-99-64, pp. 1-10 (1975).

Miyata, J., and Nakahara, K., "On-site Water Quality Monitoring Technology for Wastewater Treatment Plants," JFE Technical Report, No. 9, pp. 31-36 (Mar. 2007).

Parkash, J., et al., "Depolarized Resonance Light Scattering by Porphyrin and Chlorophyll a Aggregates," Biophysical Journal, vol. 74, Issue 4, 2089-2099 (1998).

Pasternack, R. F., et al., "Porphyrin assemblies on DNA as studied by a resonance light-scattering technique," The Journal of the American Chemical Society, vol. 115, Issue 3, pp. 5393-5399 (Jun. 1993).

Rubio, S., et al., "Analytical Applications of Synchronous Fluorescence Spectroscopy," Talanta, vol. 33, Issue 8, pp. 633-640 (Aug. 1986).

Shang, L., and Dong, S., "Detection of neurotransmitters by a light scattering technique based on seed-mediated growth of gold nanoparticles," Nanotechnology, vol. 19, Issue 9, pp. 095502-1-095502-6 (Feb. 11, 2008).

Vo-Dinh, T., "Multicomponent Analysis by Synchronous Luminescence Spectrometry," Analytical Chemistry, vol. 50, Issue 3, pp. 396-401 (Mar. 1978).

Weng, G., et al., "Decreased resonance light scattering of citrate-stabilized gold nanoparticles by chemisorption of mercaptoacetic acid," Colloids and Surfaces A: Physicochemical and Engineering Aspects, vol. 369, Issue 1-3, pp. 253-259 (Oct. 20, 2010).

\* cited by examiner

SYSTEMS AND METHODS FOR LIQUID
QUALITY ASSESSMENT

CROSS-REFERENCE TO RELATED APPLICATION

The present application is a U.S. National Stage Application under 35 U.S.C. §371 of International Application Serial No. PCT/IB2014/063798, filed on Aug. 8, 2014, which claims priority under 35 U.S.C. §119 to IN Application No. 943/KOL/2013, filed on Aug. 9, 2013, the entire contents of which are incorporated herein by reference.

BACKGROUND

The following description is provided to assist the understanding of the reader. None of the information provided or references cited is admitted to be prior art.

Assessment of liquid quality, for example, water quality and organic solvent quality, is important and frequently performed. Many types of water systems require monitoring and testing, including drinking water systems, wastewater facilities, natural water bodies, field irrigation systems, groundwater monitoring systems, and public swimming beaches and pools. Assessment of non-aqueous liquids, for example, organic solvents, is used in chemical and pharmaceutical industries. Types of data that require monitoring include physical and chemical liquid quality parameters, radiological liquid quality parameters, microbiological liquid quality parameters, and so on. There is an increasing need for rapid, simple, and real-time systems and methods for liquid quality testing throughout the world.

SUMMARY

The present technology provides an illustrative liquid quality assessment system. The system includes a light source configured to illuminate a liquid sample, a reflecting surface configured to reflect light scattered by the liquid sample, and a detector configured to detect light intensity. The light source is configured to illuminate the liquid sample with a first incident light when the reflecting surface is absent and illuminate the liquid sample with a second incident light when the reflecting surface is present. The detector is configured to detect a first light scattered by the liquid sample in response to the first incident light and detect a second light which is a combination of light scattered by the liquid sample in response to the second incident light and light reflected by the reflecting surface of light scattered by the liquid sample in response to the second incident light.

The present technology also provides an illustrative method of assessing liquid quality. The method includes providing a first incident light to a liquid sample in an absence of a reflecting surface, detecting a first scattering intensity of a first light scattered by the liquid sample in response to the first incident light in the absence of the reflecting surface, providing a second incident light to the liquid sample in a presence of the reflecting surface, detecting a second scattering intensity of a second light which is a combination of light scattered by the liquid sample in response to the second incident light and light reflected by the reflecting surface of light scattered by the liquid sample in response to the second incident light, and assessing quality of the liquid sample by comparing the second scattering intensity to the first scattering intensity.

The present technology also provides an illustrative liquid quality assessment system that includes a light source configured to provide polarized excitation light to a liquid sample. The system further includes a detector configured to detect polarized emission light emitted by the liquid sample in response to the polarized excitation light.

The present technology further provides an illustrative method of assessing quality of a liquid sample that includes providing a polarized excitation light to the liquid sample and detecting a polarized emission light emitted by the liquid sample in response to the polarized excitation light. The method further includes assessing quality of the liquid sample from the polarized emission light that is detected.

The present technology further provides an illustrative method of measuring concentration of a biological impurity in a liquid sample. The method includes providing a polarized excitation light to the liquid sample, detecting a polarized emission light emitted by the liquid sample in response to the polarized excitation light, wherein a difference between a wavelength of the emission light and a wavelength of the excitation light is fixed, and assessing the concentration of the biological impurity in the liquid sample from the polarized emission light that is detected.

The present technology also provides an illustrative method of measuring concentrations of one or more ionic impurities in a liquid sample. The method includes treating a first liquid sample from a liquid source with a first chelator specific to a first ionic impurity, providing a first incident light to the first liquid sample in an absence of a reflecting surface, detecting a first scattering intensity of a first light scattered by the first liquid sample in response to the first incident light in the absence of the reflecting surface. The method further includes providing a second incident light to the first liquid sample in a presence of the reflecting surface, detecting a second scattering intensity of a second light which is a combination of light scattered by the liquid sample in response to the second incident light and light reflected by the reflecting surface of light scattered by the first liquid sample in response to the second incident light, assessing the concentration of a second ionic impurity in the first liquid sample by comparing the second scattering intensity to the first scattering intensity.

The present technology further provides an illustrative method of measuring concentration of one or more ionic impurities in a liquid sample. The method includes providing a first polarized excitation light to the liquid sample, detecting a first polarized emission light emitted by the liquid sample in response to the first polarized excitation light, wherein a first difference between a wavelength of the emission light and a wavelength of the excitation light according to a first ionic impurity is fixed, assessing the concentration of the first ionic impurity in the liquid sample from the first polarized emission light that is detected.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are; therefore, not to be considered limiting of its scope, the disclosure will be described with additional specificity and detail through use of the accompanying drawings.

DETAILED DESCRIPTION

Figure 1:
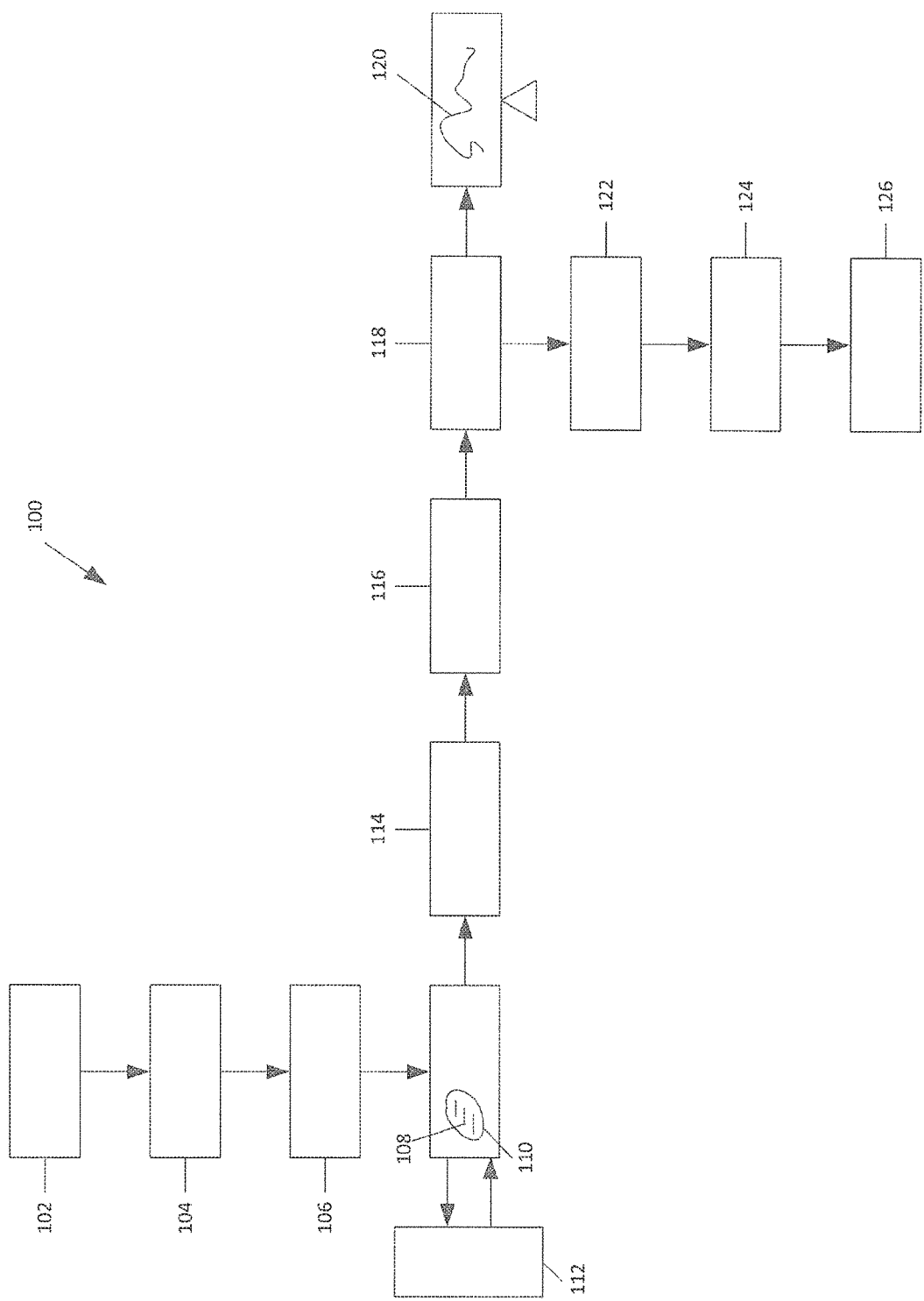
FIG. 1 depicts a liquid quality assessment system in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

When light is incident on a particle, it is scattered in all directions. The scattering may take the form of Rayleigh scattering, Mie scattering, or other forms of scattering. Rayleigh scattering is an elastic process, by which light can be deviated from its path with no change in wavelength. The particle may absorb the incident light and emit energy as light, or as "fluorescence." Emitted light from the particle may typically have a different wavelength than the incident light that is absorbed by the particle. Properties and concentrations of the particle can be investigated by measuring the spectra of the scattered light and/or the fluorescence.

FIG. 1 depicts a liquid quality assessment system 100 in accordance with an illustrative embodiment. Liquid quality assessment system 100 includes a light source 102 configured to illuminate a liquid sample 108 with incident light. In an embodiment, light source 102 includes a Xenon lamp and liquid sample 108 is water. In alternative embodiments, light source 102 may include white LEDs, white lasers, multi-spectrum light emitters, or any other appropriate light sources known to those skilled in the art. In addition, in additional embodiments, liquid sample 108 may include liquids other than water such as non-aqueous liquids, organic solvents, or any other liquids applicable to such a system.

In an embodiment, the incident light is provided over a wavelength of about 200 nm to about 800 nm. In an alternative embodiment, the wavelength is about 300 nm to about 600 nm. In a further alternative embodiment, the wavelength is about 350 nm to about 550 nm or in any other suitable wavelength range for the specific application. Specific examples of wavelengths include about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, and ranges between any two of these values (including endpoints).

In an embodiment, liquid sample 108 is maintained in a substantially static position in a sample holder 110 during the illumination by light source 102. In an embodiment, the amount of liquid is one milliliter (ml). In alternative embodiments, the amount of liquid is 50 micro liters (pi) or less. In still other embodiments, the amount of liquid sample 108 may be any suitable amount for the specific application. In another embodiment, liquid sample 108 may include flowing or moving liquid. In an embodiment, liquid sample 108 is water. In another embodiment, liquid sample 108 is at least one organic solvent.

Sample holder 110 may include a material that has a high transparency to ultraviolet light such that ultraviolet light may pass through sample holder 110 to liquid sample 108. In an embodiment, sample holder 110 is made of synthetic quartz. In alternative embodiments, sample holder 110 is made of any material with high transmission efficiency with appropriate size to hold liquid sample 108. In another embodiment, sample holder 110 is a flow-through cuvette for flowing liquid.

In an embodiment, system 100 includes an excitation monochromator 104 configured to monochromatize the incident light provided by light source 102. In an embodiment, excitation monochromator 104 includes gratings as known to those of skill in the art. For example, excitation monochromator 104 may include a grating which has 1200 lines per millimeter (mm) with a 300 nm blaze. Blaze is the wavelength at which the grating is at its maximum efficiency. In another embodiment, excitation monochromator 104 includes a grating which has 1200 lines per millimeter with a blaze of about 300 nm to about 500 nm. In alternative embodiments, the grating may include an alternative suitable density of lines with an alternative suitable blaze for the specific application. In another embodiment, excitation monochromator 104 is integrated into light source 102.

In an embodiment, system 100 further includes an excitation polarizer 106 configured to polarize the incident light provided by light source 102. Excitation polarizer 106 polarizes the incident light in a particular plane. In an embodiment, a polarization direction of 0° means that the electromagnetic wave is confined to the horizontal or XY plane, while a polarization direction of 90° means that the electromagnetic wave is confined to the vertical or XZ plane. In an embodiment, excitation polarizer 106 includes a prism based polarizer, for example, a Glan Thompson polarizer. In alternative embodiments, excitation polarizer 106 includes a thin film polarizer or any other suitable polarizer known to those skilled in the art. In another embodiment, excitation polarizer 106 is integrated into light source 102.

System 100 also includes a reflecting surface 112 that is configured to reflect light scattered by liquid sample 108. In an embodiment, reflecting surface 112 is placed parallel to the propagation direction of the incident light and opposite to a detector 118. In an embodiment, reflecting surface is 0.3 centimeter (cm) away from liquid sample 108. In alternative embodiments, the distance can be varied for the specific application. The distance can be as small as near zero and can be increased to distances greater than 0.3 cm. In an embodiment, reflecting surface 112 is a plane mirror. In another embodiment, reflecting surface 112 is a polished metal surface. In alternative embodiments, reflecting surface 112 is made of other suitable reflective materials known to those of skill in the art.

In an embodiment, system 100 further includes an emission polarizer 114 configured to polarize light scattered by liquid sample 108. In an embodiment, emission polarizer 114 includes a prism based polarizer, for example, a Glan Thompson polarizer. In alternative embodiments, emission polarizer 114 may include a thin film polarizer or any other suitable polarizer known to those skilled in the art. In an alternative embodiment, emission polarizer 114 is integrated into a detector 118.

In an embodiment, system 100 also includes an emission monochromator 116 configured to monochromatize light scattered by liquid sample 108. In an embodiment, emission monochromator 116 includes gratings. For example, emission monochromator 116 may include a grating which has 1200 lines per millimeter (mm) with a 300 nm blaze. In another embodiment, emission monochromator 116 includes a grating which has 2400 lines per millimeter with a 200 nm-500 nm blaze. In alternative embodiments, the grating may include any suitable density of lines with any suitable blaze for the specific application. In another embodiment, emission monochromator 116 is integrated into detector 118. In an embodiment, to detect Rayleigh scattering or Mie scattering, emission monochromator 116 is varied synchronously with excitation monochromator 104 so that the wavelength of detected scattering light is substantially equal to the wavelength of incident light.

System 100 includes detector 118 which is configured to detect the intensity of light scattered by liquid sample 108. In an embodiment, detector 118 is configured to generate an electrical signal, or signals, representative of the intensity of light incident on detector 118. In a further embodiment, detector 118 includes a photomultiplier tube (PMT) detector. In alternative embodiments, detector 118 includes charge coupled devices (CCD) with software support or any other appropriate detector known to those skilled in the art. For example, such a CCD may include a lensless CCD-based fluorometer using a micromachined optical Soller collimator.

In an embodiment, detector 118 is configured to detect scattering light that is perpendicular to the incident light. In alternative embodiments, detector 118 can be configured to detect scattering light along any direction with sufficient sensitivity of measurement.

In an embodiment, system 100 includes a monitor 120 configured to display the scattering light intensity detected by detector 118 or to monitor the detection process. In addition, monitor 120 may include a user interface to enable user control of the detection process. In addition, monitor 120 may further display assessment results, nanoparticle measurements, graphs, messages, or other display information in accordance with output of a liquid quality assessor 126 as discussed below. In a further embodiment, monitor 120 includes a touch screen device.

In an embodiment, system 100 also includes a spectrum constructor 122 configured to construct a scattering spectrum from the scattering light intensities detected by detector 118. In an embodiment, data regarding the light intensities may be analyzed by software, such as Matlab software (MathWorks, Inc.; Natick, Mass., USA). In a further embodiment, the Matlab codes or other applicable software may be integrated into a chip that is embodied within a sensing device. In addition, the chip may be configured to communicate with a computing device and/or display such as a hand held touch screen monitor. In alternative embodiments, spectrum constructor 122 may be realized as any software, firmware, hardware, or combination thereof known to those of skill in the art.

In an embodiment, system 100 further includes a spectrum analyzer 124 that is configured to analyze spectra based on scattering light generated in the presence and absence of reflecting surface 112 as constructed by spectrum constructor 122. In an embodiment, spectrum analyzer 124 identifies positions of peaks, for example over a wavelength range of about 350 nm to about 550 nm, for both spectra based on scattering light generated in the presence and absence of reflecting surface 112, and calculates ratios of intensities of one or more peaks in the spectrum for scattering light formed in the presence of reflecting surface 112 to the intensities of the one or more peaks in the spectrum for scattering light formed in the absence of reflecting surface 112. The wavelength range is adjusted according to types of impurities to be detected, for example, specific nanoparticles, proteins, and other impurities. In an embodiment, the calculation of the ratios of intensities by the spectrum analyzer 124 includes determining an enhancement factor, which is the ratio of the intensity of the highest peak in the presence of reflecting surface 112 to the intensity of the highest peak in the absence of reflecting surface 112. In another embodiment, the calculation of the ratios of intensities by the spectrum analyzer 124 includes determining a quality factor, which is the average of ratios of intensities of peaks in the presence of reflecting surface 112 to the intensities of peaks in the absence of reflecting surface 112.

In an embodiment, spectrum analyzer 124 is realized as software. In a further embodiment, codes and/or software are integrated into a chip that is embodied with a computing device. In addition, the chip may be configured to communicate with a display such as a hand held touch screen monitor. In alternative embodiments, spectrum analyzer 124 may be realized as any software, firmware, hardware, or combination thereof known to those skilled in the art.

System 100 further includes a liquid quality assessor 126 configured to assess the quality of liquid sample 108 based on the output of spectrum analyzer 124. For example, in an embodiment, liquid quality assessor 126 compares the enhancement factor obtained by spectrum analyzer 124 to a predetermined threshold that corresponds to a given quality of a liquid sample. In another embodiment, liquid quality assessor 126 compares the quality factor to a predetermined threshold. Based on the given comparison, liquid quality assessor 126 determines the quality of the liquid sample. For example, in an embodiment, when the enhancement factor as calculated by spectrum analyzer 124 is at least 200%, liquid quality assessor 126 determines that the liquid sample is "substantially ion free" by comparing the enhancement factor to a predetermined threshold in a stored lookup table that indicates as such. In alternative embodiments, indications may be adjusted according to types of impurities to be detected, for example, the indication may be "substantially nanoparticles free" or "substantially protein free."

In an embodiment, liquid quality assessor 126 provides an indicator indicating ionic level of liquid sample 108. In an embodiment, a look-up table is generated by measuring liquid samples with different known ionic levels. In a further embodiment, the codes are integrated into a chip that is embodied in a computing and/or detection device. In addition, the chip may be configured to communicate with a display such as a hand held touch screen monitor. In alternative embodiments, liquid quality assessor 126 may be realized as any software, firmware, hardware, or combination thereof known to those skilled in the art.

In a further embodiment, system 100 may be calibrated by using liquid samples obtained by adding sodium chloride (NaCl) or other standard ionic compounds at different concentrations to Millipore water (or purified water from other standard instruments). In alternative embodiments, laser Doppler velocimetry or portable conductivity meters may be used to provide an estimation of ionic level and to ensure that liquid quality assessor 126 provides an accurate result.

Figure 2:
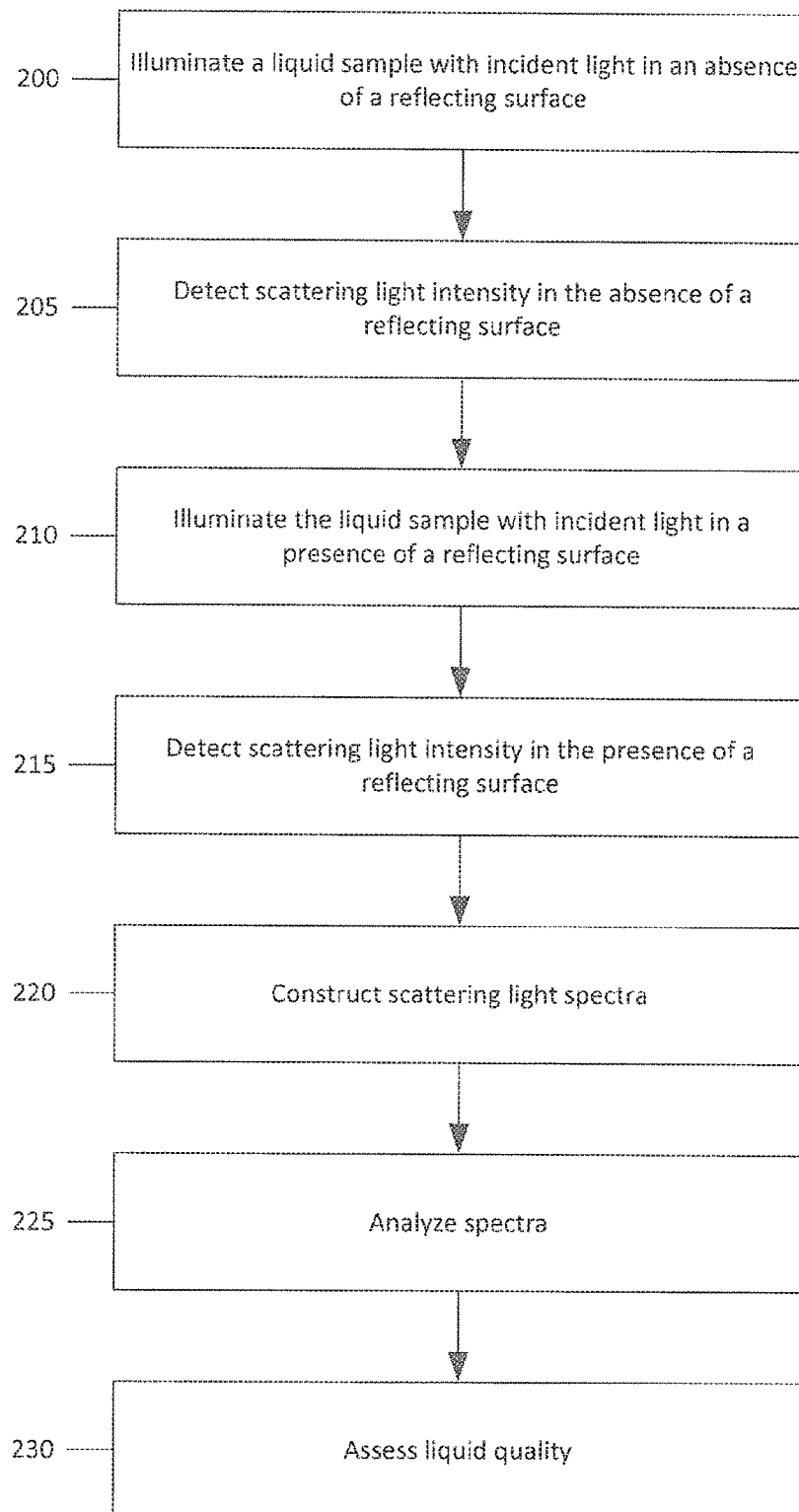
FIG. 2 depicts a flow diagram of a liquid quality assessment method in accordance with an illustrative embodiment.

FIG. 2 depicts a flow diagram of a liquid quality assessment method in accordance with an illustrative embodiment. In an operation 200 (Illuminate a liquid sample with incident light in an absence of a reflecting surface), a light source illuminates a liquid sample with incident light in the absence of a reflecting surface. In an embodiment, the incident light is monochromatized by a monochromator. In further embodiments, the incident light may be polarized or unpolarized. In an embodiment, the incident light is provided over a wavelength range of about 200 nm to about 800 nm. In an alternative embodiment, the wavelength range is about 300 nm to about 600 nm. In a further alternative embodiment, the wavelength range is about 350 nm to about 550 nm. The incident light is not limited to the ranges identified. Those skilled in the art may adjust the wavelength range as desired for the specific application.

In an operation 205 (Detect scattering light intensity in the absence of a reflecting surface), the intensity of light scattered by the liquid sample in the absence of a reflecting surface is detected. In an embodiment, the intensity of Rayleigh scattering light is detected. In an alternative embodiment, the intensity of Mie scattering may be detected. During detection of the intensity of the scattered light, the liquid sample may be contained in a static position within a transparent container. In an alternative embodiment, a flowing or moving liquid sample may be analyzed as well.

In an operation 210 (Illuminate the liquid sample with incident light in a presence of a reflecting surface), the light source illuminates the liquid sample with incident light in the presence of a reflecting surface. In an embodiment, the reflecting surface is placed parallel to the propagation direction of the incident light and opposite to a detector. In an embodiment, the reflecting surface is a plane mirror. In another embodiment, the reflecting surface is a polished metal surface. In alternative embodiments, the reflecting surface is made of any other suitable reflective materials known to those of skill in the art. In various embodiments, the incident light may be polarized or unpolarized.

In an operation 215 (Detect scattering light intensity in the presence of a reflecting surface), the intensity of light, which is a combination of light scattered by the liquid sample in response to the incident light and light reflected by the reflecting surface of light scattered by the liquid sample in response to the incident light, is detected. In alternative embodiments, different combinations of polarization directions for incident/scattering lights may be used. For example, the incident/scattering polarization directions may be 90°/0°, 90°/90°, 0°/0°, 0°/90°, or other combinations, depending on the specific embodiment.

The method may further include an operation 220 (Construct scattering light spectra). In operation 220, scattering light spectra are constructed based on the detected scattering light intensities both in the presence and absence of the reflecting surface. For example, the intensity of the scattering light may be determined at each wavelength and a spectrum of the intensities at each wavelength constructed in a graph or other format. In an embodiment, software such as Matlab software may be used to analyze the raw data to construct the spectra. In a further embodiment, the Matlab codes or other software are integrated into a chip that is embodied in a computing and/or detection device. In addition, the chip may be configured to communicate with a display such as a hand held touch screen monitor. In alternative embodiments, any software, firmware, hardware, or combination thereof known to those of skill in the art may be used to construct the spectra.

The method may also include an operation 225 (Analyze spectra). In operation 225, scattering light spectra both in the presence and absence of the reflecting surface are analyzed. In an embodiment, to determine an ionic level of the liquid sample, positions of highest peaks over a wavelength range, for example, about 350 nm to about 550 nm, for both spectra are identified and an enhancement factor is determined. The enhancement factor is the ratio of the intensity of the highest peak in the spectrum for scattering light formed in the presence of the reflecting surface to the intensity of the highest peak in the spectrum for scattering light formed in the absence of the reflecting surface are calculated. In another embodiment, a quality factor may be determined, which is the average of ratios of intensities of peaks in the presence of the reflecting surface to the intensities of peaks in the absence of the reflecting surface. In an alternative embodiment, the wavelength range is adjusted according to the type(s) of impurities to be detected, for example, specific nanoparticles, proteins, and so on. In an embodiment, software is used to analyze the spectra. In a further embodiment, the codes and/or software are integrated into a chip embodied with a computing and/or detection device. In addition, the chip may be configured to communicate with a display such as a hand held touch screen monitor. In alternative embodiments, any software, firmware, hardware, or combination thereof known to those skilled in the art may be used to analyze the spectra.

The method may further include an operation 230 (Assess liquid quality). In operation 230, the quality of the liquid sample is assessed based on the output of operation 225. In an embodiment, the enhancement factor is compared to predetermined values that correspond to known ionic levels of a given impurity using, for example, a stored look-up table. In another embodiment, the quality factor is compared to predetermined values. In a further embodiment, a look-up table is generated by measuring liquid samples with different known ionic levels. For example, liquid samples that are used to calibrate are obtained by adding sodium chloride (NaCl) or other standard ionic compounds at different concentrations to purified liquid. In an alternative embodiment, laser Doppler velocimetry or portable conductivity meters may be used to provide an estimation of ionic level and the present method gives an accurate result.

In an example embodiment, when the enhancement factor is at least 200%, the detection device determines that the liquid sample is "substantially ion free" as indicated by the look-up table for the given ratio. In another embodiment, an indicator indicating a specific ionic level of the liquid sample is provided. In alternative embodiments, indications may be adjusted according to types of impurities to be detected. In an embodiment, software is used to assess the liquid quality. In a further embodiment, the codes and/or software are integrated into a chip that is embodied in a computing or detection device. In addition, the chip may be configured to communicate with a display such as a hand held touch screen monitor. In alternative embodiments, any software, firmware, hardware, or combination thereof known to those skilled in the art may be used to assess liquid quality.

Figure 3:
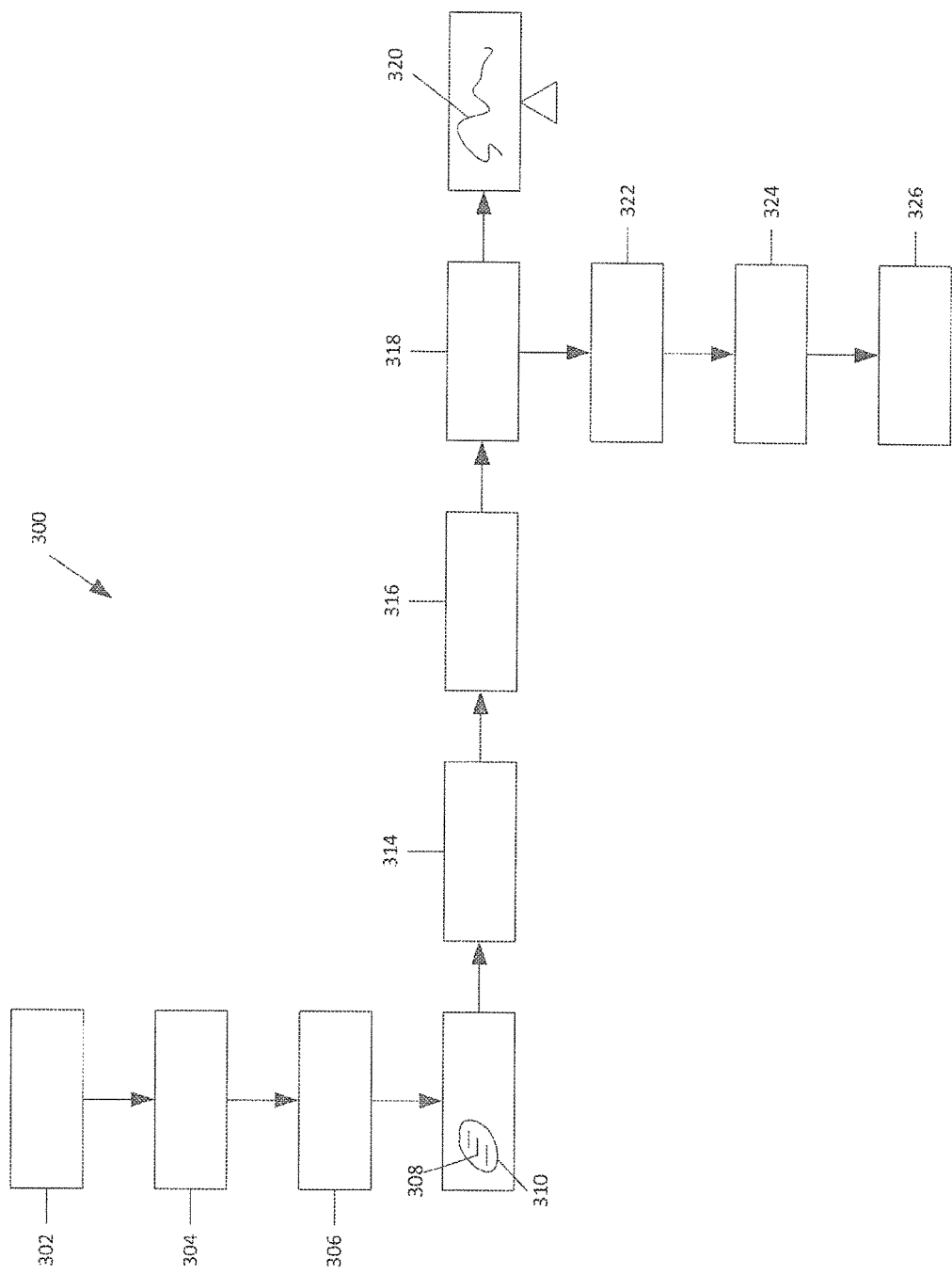
FIG. 3 depicts a liquid quality assessment system in accordance with another illustrative embodiment.

FIG. 3 depicts a liquid quality assessment system 300 in accordance with an illustrative embodiment. Liquid quality assessment system 300 includes a light source 302 configured to provide incident light to a liquid sample 308 in a sample holder 310. Light source 302, liquid sample 308, and sample holder 310 are similar to light source 102, liquid sample 108, and sample holder 110, respectively, as described above with respect to system 100.

In an embodiment, system 300 includes an excitation monochromator 304 configured to monochromatize the incident light provided by light source 302 and an excitation polarizer 306 configured to polarize the incident light provided by light source 302.

In an embodiment, system 300 further includes an emission polarizer 314 configured to polarize light emitted by liquid sample 308 in response to the incident light, and an emission monochromator 316 configured to monochromatize light emitted by liquid sample 308. In an embodiment, to detect intensity of the light emitted by liquid sample 308, for example fluorescence intensity, excitation monochromator 304 and emission monochromator 316 vary the excitation wavelength and the emission wavelength of light, respectively, while maintaining a fixed difference between the excitation wavelength and the emission wavelength. In a further embodiment, the difference between emission wavelength and excitation wavelength, $\Delta\lambda$, is maintained at approximately 60 nm while the emission and excitation wavelengths are varied across the applicable wavelength range. In alternative embodiments, the wavelength difference $\Delta\lambda$ may be adjusted according to impurities, for example biological substances to be detected.

System 300 includes a detector 318 configured to detect intensity of light (for example, fluorescence) emitted by liquid sample 308. Detector 318 is similar to detector 118 as described above with respect to system 100. In an embodiment, system 300 also includes a monitor 320 similar to monitor 120 in system 100.

In an embodiment, system 300 also includes a spectrum constructor 322 configured to construct a polarized emission spectrum from the intensities of emitted light detected by detector 318. In an embodiment, the intensities of the emitted light correspond to intensities of emitted fluorescence. The constructed spectrum describes respective intensities of emitted light at various wavelengths. In an embodiment, data regarding intensities of emitted light may be analyzed by software such as Matlab software. In a further embodiment, the Matlab codes and/or other suitable software may be integrated into a chip embodied with a computing and/or detecting device. In addition, the chip may be configured to communicate with a display such as a hand held touch screen monitor. In alternative embodiments, spectrum constructor 322 may be realized as any software, firmware, hardware, or combination thereof known to those of skill in the art.

In an embodiment, system 300 further includes a spectrum analyzer 324 configured to identify the position and intensity of emission peaks from the emission spectrum. In an embodiment, to detect silica, emission peaks are identified over a wavelength range of about 300 nm to about 500 nm. In alternative embodiments, the wavelength range may be adjusted according to the emission, for example fluorescence, nature of the specific impurities to be detected. In an embodiment, spectrum analyzer 324 is realized as software. In a further embodiment, codes and/or software is integrated into a chip embodied within a computing or detection device. In addition, the chip may be configured to communicate with a display such as a hand held touch screen monitor. In alternative embodiments, spectrum analyzer 324 may be realized as any software, firmware, hardware, or combination thereof known to those skilled in the art.

In an embodiment, system 300 includes a liquid quality assessor 326 configured to assess the quality of liquid sample 308 based on the identified emission (for example, fluorescence) peaks. In an embodiment, liquid quality assessor 326 determines the impurity concentration of liquid sample 308 by comparing the identified emission peaks (for example, positions of the peaks, intensities of the peaks and other characteristics of the spectrum) to predetermined relationships between emission peaks and impurity concentrations using, for example, a stored look-up table. The predetermined relationships may be illustrated by a curve. In alternative embodiments, the predetermined relationships may include data other than a curve.

In an embodiment, the impurity to be detected is soluble silica. In alternative embodiments, the impurity may include biological, inorganic, or organic impurities. For example, the specific impurity may also include an antibody, a dendrimer, or a similar entity with a fluorescent tage. In an embodiment, liquid quality assessor 326 is realized as software. In a further embodiment, the codes and/or software may be integrated into a chip embodied within a computing or detection device. In addition, the chip may be configured to communicate with a display such as a hand held touch screen monitor. In alternative embodiments, liquid quality assessor 326 may be realized as any software, fir e, hardware, or combination thereof known to those skilled in the art.

Figure 4:
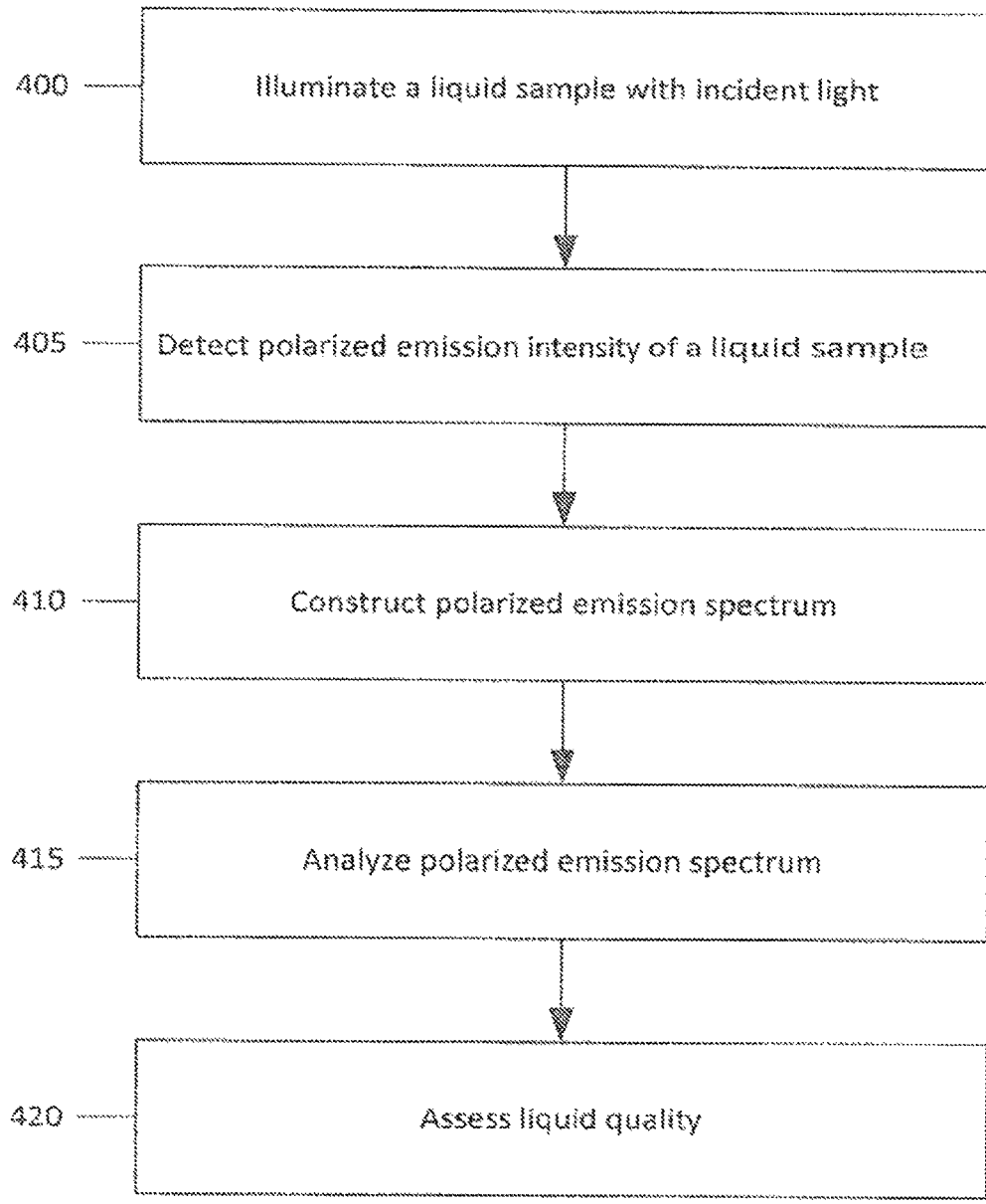
FIG. 4 depicts a flow diagram of a liquid quality assessment method in accordance with another illustrative embodiment.

FIG. 4 depicts a flow diagram of a liquid quality assessment method in accordance with another illustrative embodiment. In an operation 400 (Illuminate a liquid sample with polarized incident light), a light source illuminates a liquid sample with polarized incident light. In an embodiment, the incident light is monochromatized by a monochromator and polarized by a polarizer. In an embodiment, the incident light is provided over a wavelength range of about 300 nm to about 500 nm. In another embodiment, incident light is provided over a wavelength range of about 200 nm to about 800 nm. In still further embodiments, the wavelength range may be adjusted according to the fluorescence nature of impurities to be detected. Those skilled in the art may adjust the wavelength range as desired for the specific application.

In an operation 405 (Detect polarized emission intensity of a liquid sample), the emission intensity, for example, synchronous fluorescence intensity, of a liquid sample is detected. To measure emission intensity, the excitation wavelength and the emission wavelength are varied synchronously while the difference between the excitation wavelength and the emission wavelength, $\Delta\lambda$ (delta lambda), is fixed. In an embodiment, $\Delta\lambda$ is approximately 60 nm. In alternative embodiments, $\Delta\lambda$ may be adjusted according to the fluorescence nature of impurities to be detected. In various embodiments, different combinations of excitation/emission polarization directions may be used. For example, the combination of polarization directions of excitation/emission lights is 90°/0°, 90°/90°, 0°/0°, 0°/90°, or other combinations, in different embodiments.

In an operation 410 (Construct polarized emission spectrum), a polarized emission spectrum is constructed based on the detected polarized emission intensities. In an embodiment, software such as Matlab software may be used to analyze the raw data to construct the spectrum. In a further embodiment, the Matlab codes and/or software are integrated into a chip embodied within a computing and/or detection device. In addition, the chip may be configured to communicate with a display such as a hand held touch screen monitor. In alternative embodiments, any software, firmware, hardware, or combination thereof known to those skilled in the art may be used to construct the spectrum.

The method further includes an operation 415 (Analyze polarized emission spectrum). In operation 415, the position and the intensity of emission peaks are identified. In an embodiment, the spectrum is analyzed by a computing device using software. In alternative embodiments, the codes and/or software may be integrated into a chip embodied in a computing and/or detection device. In addition, the chip may be configured to communicate with a display such as a hand held touch screen monitor. In alternative embodiments, any software, firmware, hardware, or combination thereof known to those skilled in the art may be used to analyze the spectrum.

In an operation 420 (Assess liquid quality), the quality of the liquid sample is assessed based on the identified intensity of the fluorescence peak. In an embodiment, an indicator indicating an impurity concentration of the liquid sample being tested is provided. The impurity to be detected may be soluble silica. In other embodiments, the impurity to be detected may be a biological, inorganic, or organic impurity, such as antibodies or dendrimers, or any other suitable impurity applicable to such a liquid quality assessment system.

In an embodiment, the impurity concentration of the liquid sample is determined by comparing the identified intensity of the emission peak (for example, positions of the peaks, intensities of the peaks and other characteristics of the spectrum) to a look-up table that stores predetermined relationships between respective emission peak intensities and corresponding impurity concentrations. The predetermined relationships may be illustrated by a curve or any other mechanism known to those of skill in the art. In an embodiment, liquid quality is assessed by a device using software embodied within the device. In alternative embodiments, the codes and/or software are integrated into a chip embodied within a computing and/or detection device. In addition, the chip may be configured to communicate with a display such as a hand held touch screen monitor. In alternative embodiments, any software, firmware, hardware, or combination thereof known to those skilled in the art may be used to assess liquid quality.

The methods and systems as described in the embodiments above can be used to detect and measure concentrations of a biological impurity in a liquid sample, for example, a water sample. In an embodiment, the method may include providing a polarized excitation light to the liquid sample, and detecting a polarized emission light emitted by the liquid sample in response to the polarized excitation light. A fixed difference between a wavelength of the emission light and a wavelength of the excitation light can be maintained. The fixed difference may vary with different biological impurities. For example, where the biological impurity is a protein impurity, the fixed difference can be about 50 nm. Also, where the biological impurity is a bacterial impurity, the fixed difference can be about 100 nm to about 110 nm. The method may further include assessing the concentration of the biological impurity in the liquid sample from the polarized emission light that is detected. The assessment can be performed by analyzing an emission spectrum that is constructed based on the detected polarized emission light. The emission intensity peaks and positions in the spectrum can be compared to pre-determined relationships of emission peaks with concentrations of various biological impurities to determine the concentrations of the detected biological impurities.

The methods and systems as described in the disclosed embodiments can also be used to detect and measure concentrations of one or more ionic impurities in a liquid sample from a liquid source, for example a water sample from a water source. In one embodiment, the method may include providing a first incident light to a first liquid sample from the liquid source in an absence of a reflecting surface, and detecting a first scattering intensity of a first light scattered by the liquid sample in response to the first incident light in the absence of the reflecting surface. To increase sensitivity of the detection, for example, detecting a second ionic impurity from a liquid sample containing at least the second ionic impurity and a first ionic impurity, the first liquid sample may be pre-treated with a chelator specific to an ionic impurity that is not the focus of that detection, for example, the first ionic impurity. Accordingly, in an embodiment, the method may further include treating the first liquid sample with a first chelator specific to the first ionic impurity. For example, the ionic impurity may include Si, Pb, Ca, As, or Mg, and the chelator that is used would be specific to the respective ionic impurity. In another example embodiment, the impurity may be a sugar. In an embodiment, the method may further include providing a second incident light to the first liquid sample in a presence of the reflecting surface, and detecting a second scattering intensity of a second light which is a combination of light scattered by the liquid sample in response to the second incident light and light reflected by the reflecting surface of light scattered by the liquid sample in response to the second incident light.

To determine the concentration of the second ionic impurity in the first liquid sample which is treated with the first chelator specific to the first ionic impurity, the second scattering intensity can be compared with the first scattering intensity. For example, scattering intensities derived from scattering light formed in the presence and absence of the reflecting surface can be used to construct scattering spectra as described in the disclosed embodiments. An enhancement factor can then be determined according to the methods as described in the disclosed embodiments, and compared to a pre-determined relationship between the enhancement factor and the second ionic impurity to determine the concentration of the second ionic impurity in the liquid sample.

To detect and measure additional ionic impurities in the liquid sample, one or more additional liquid samples may be obtained from the same liquid source as the first liquid sample. The method of determining the concentration of the first ionic impurity in a second liquid sample from the same liquid source, or additional ionic impurities in additional liquid samples, can be similar to that used to measure the concentration of the second ionic impurity in the first liquid sample. In an embodiment, to measure the concentration of the first ionic impurity in the second liquid sample, the method may further include treating the second liquid sample with a second chelator specific to the second ionic impurity, providing a third incident light to the second liquid sample in an absence of the reflecting surface, detecting a third scattering intensity of a third light scattered by the second liquid sample in response to the third incident light in the absence of the reflecting surface, providing a fourth incident light to the second liquid sample in a presence of the reflecting surface, and detecting a fourth scattering intensity of a fourth light which is a combination of light scattered by the second liquid sample in response to the fourth incident light and light reflected by the reflecting surface of light scattered by the second liquid sample in response to the fourth incident light. The concentration of the first ionic impurity can then be determined in accordance with the methods as described for the first liquid sample.

In another example of detecting and measuring concentrations of one or more ionic impurities using the methods and systems as described in the disclosed embodiments, the method may include providing a first polarized excitation light to the liquid sample, and detecting a first polarized emission light emitted by the liquid sample in response to the first polarized excitation light. The liquid sample can, for example, be a water sample. A first fixed difference between a wavelength of the polarized emission light and a wavelength of the polarized excitation light can be maintained. The fixed difference can vary for different ionic impurities. The concentration of a first ionic impurity in the liquid sample can be determined from the first polarized emission light that is detected. An emission spectrum can be constructed based on the detected first polarized emission light. Positions and intensities of the emission peaks in the spectrum can then be compared to pre-determined relationships of emission peaks and various types of ionic impurities concentrations, to determine the concentration of the first ionic impurity in the liquid sample.

To detect and measure concentrations of a second and additional ionic impurities in the liquid sample, the method can be similar to that used for first ionic impurity. In an embodiment, the method may further include providing a second polarized excitation light to the liquid sample, and detecting a second polarized emission light emitted by the liquid sample in response to the second polarized excitation light. A second fixed difference between a wavelength of the emission light and a wavelength of the excitation light may be maintained. As the fixed difference varies with different ionic impurities, the second fixed difference may be different from the first fixed difference where the second ionic impurity is of a different ionic species from the first ionic impurity. The concentration of the second ionic impurity in the liquid sample can be determined from the second polarized emission light according to the methods as described for the first ionic impurity.

EXAMPLES

The following examples illustrate results produced using the systems and methods described herein.

Example 1

Rayleigh Light Scattering Spectra of Five Different Water Samples

A 72 watt Xenon lamp was used as a light source and illuminated a 1 ml static water sample contained in a synthetic quartz container with an incident light. The incident light was provided over a wavelength range of about 200 nm to about 800 nm. The water sample scattered light in response to the incident light and emitted the scattered light. The incident light and the scattered light were monochromatized by gratings which have 1200 lines per mm and a 300 nm blaze. Polarizers were used to polarize the incident light and the scattered light. The polarizers were Glan Thompson polarizers. A photomultiplier tube (PMT) detector was used to detect the intensity of the scattered light. A mirror was used as a reflecting surface, which was about 0.3 cm away from the water sample, at a side opposite to the detector. The reflecting surface of the mirror was parallel to the propagation direction of the incident light. When the reflecting surface was absent, the incident light was unpolarized. When the reflecting surface was applied, the incident light was polarized. Scattering intensities derived from scattered light formed in the presence and absence of the reflecting surface were detected, and scattering spectra were constructed accordingly.

Five different water samples were tested, namely, distilled Millipore milli-Q water, distilled water, brand 'K' water, and two tap waters from different sources. Matlab codes embodied within a detector were used to construct the scattering spectra.

Figure 5:
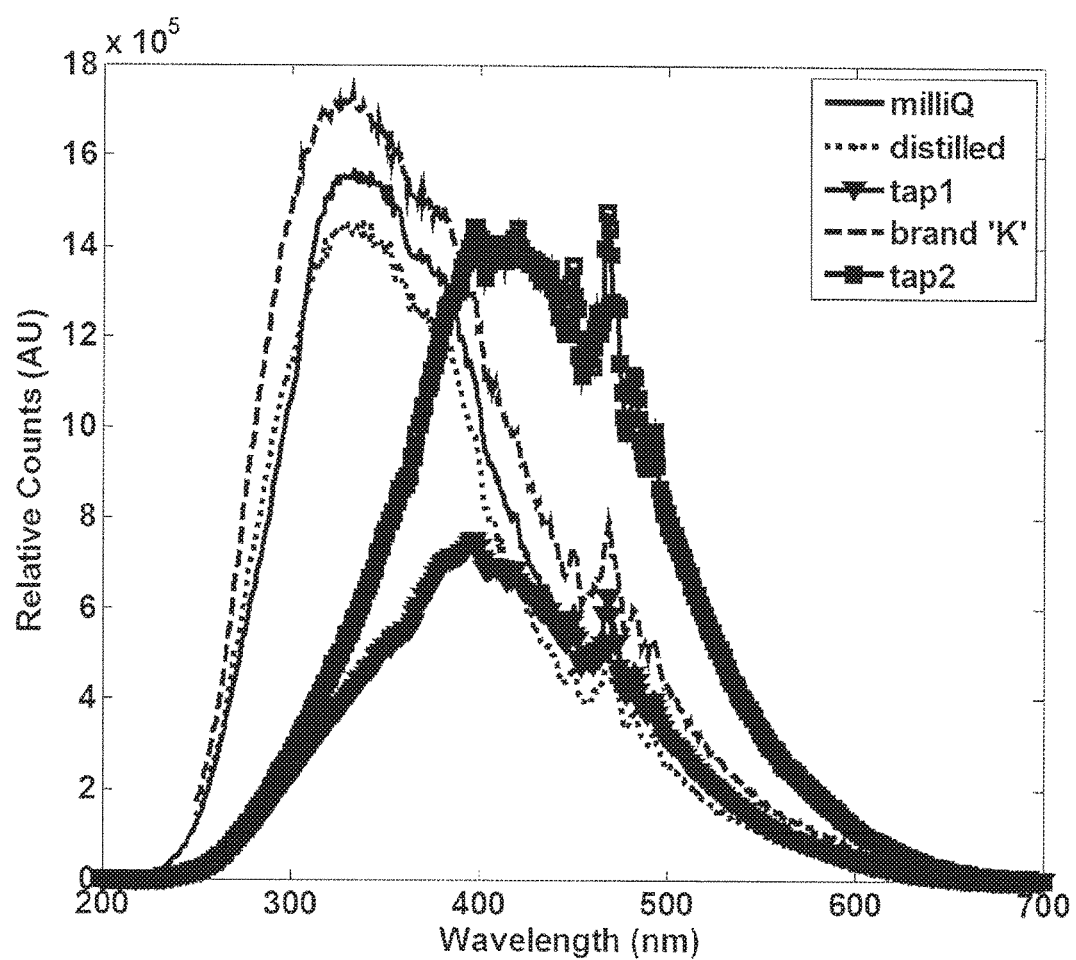
FIG. 5 is a graph illustrating Rayleigh Light Scattering (RLS) spectra of five different water samples irradiated with unpolarized light in the absence of a reflecting surface in accordance with an illustrative embodiment. The x-axis is wavelength in nanometers (nm). The y-axis is light intensity in AU.

FIG. 5 is a graph illustrating Rayleigh Light Scattering (RLS) spectra of the five different water samples irradiated with unpolarized light in the absence of the reflecting surface. As detailed in FIG. 5, unpolarized light showed resonance Rayleigh peaks at 334 nm and 375 nm for milli-Q water, filtered distilled water, and water 'K' respectively. Whereas for the two tap waters, no peaks were observed in this region, but a hump at 382 nm and a distinct peak at 392 nm were found. In FIG. 5, in order to compare spectra for the five water samples in one graph, intensities for milli-Q water, distilled water and brand 'K' water were multiplied by 4 because the tap waters showed higher intensities.

FIGS. 6-9 are graphs illustrating normalized difference RLS spectra of the five different water samples irradiated with polarized light under different combinations of incident/scattering polarization directions in the presence of the reflecting surface. A normalized difference spectrum is a spectrum normalized by the maximum of the differences between intensities in the presence of the reflecting surface and in the absence of the reflecting surface. For example, to obtain a normalized intensity, a difference between intensities in the presence of the reflecting surface and in the absence of the reflecting surface at a wavelength is calculated. The difference is then divided by the maximum of the differences between intensities in the presence of the reflecting surface and in the absence of the reflecting surface over the whole wavelength range. The normalized intensity is obtained by multiplying the divided difference with the enhancement factor f. The enhancement factor f is the ratio of the intensity of the highest peak in the presence of the reflecting surface to the intensity of the highest peak in the absence of the reflecting surface.

Figure 6:
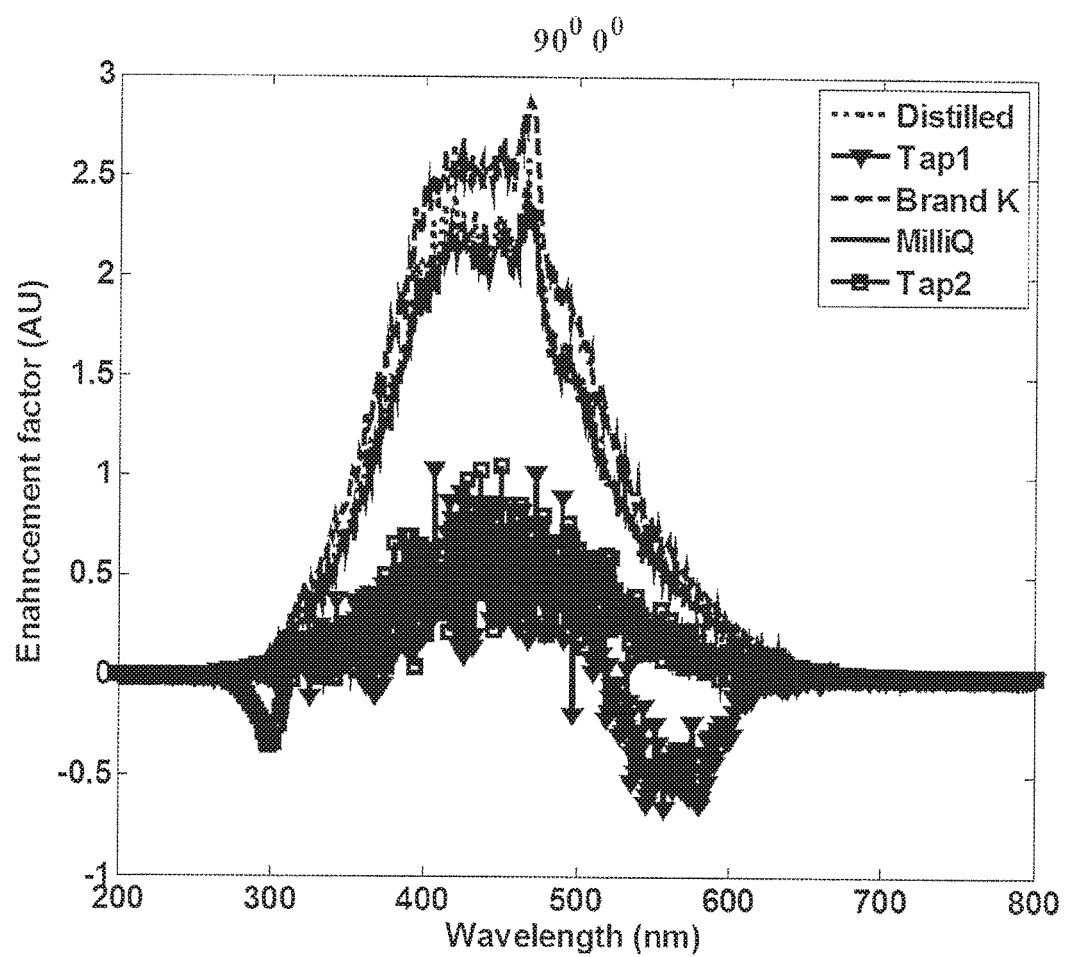
FIG. 6 is a graph illustrating normalized difference RLS spectra of five different water samples irradiated with polarized light in the presence of a reflecting surface, where polarization direction of the incident light is 90° and polarization direction of the scattering light is 0° in accordance with an illustrative embodiment. The x-axis is wavelength in nanometers (nm). The y-axis is enhancement factor in AU.
Figure 7:
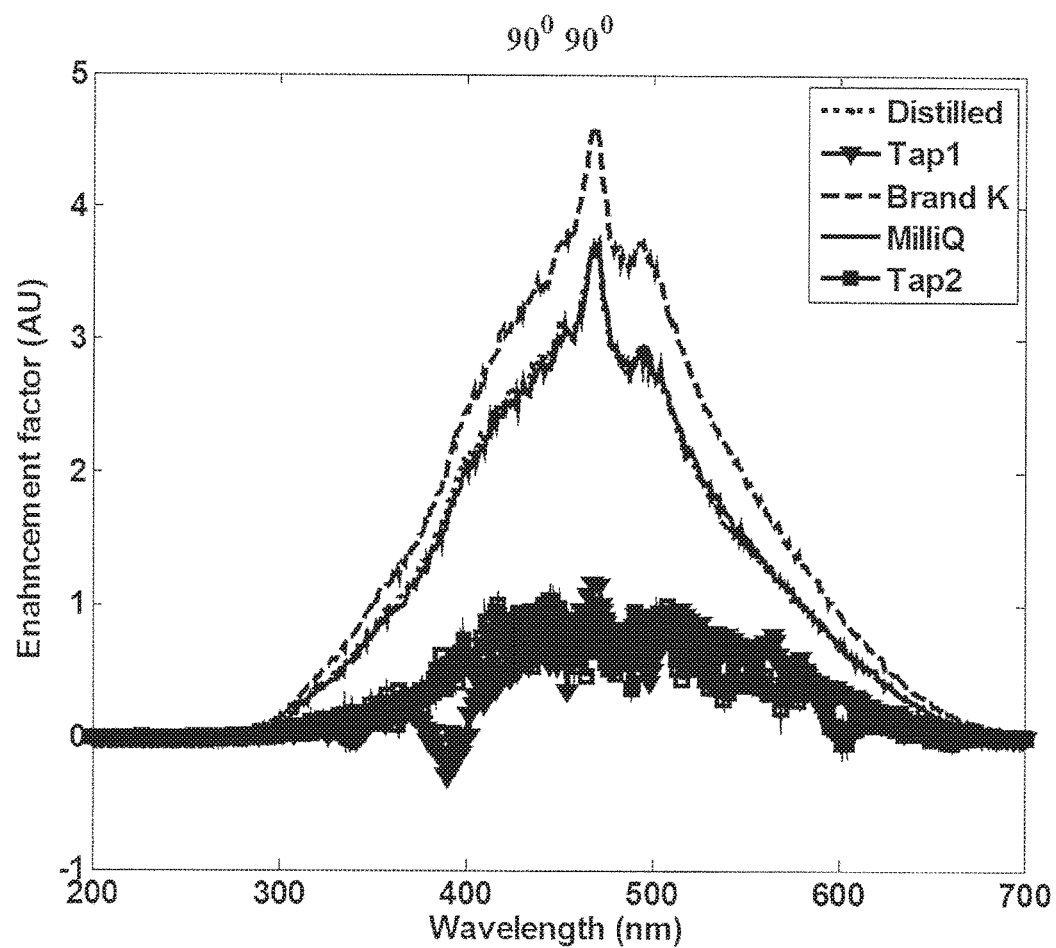
FIG. 7 is a graph illustrating normalized difference RLS spectra of five different water samples irradiated with polarized light in the presence of a reflecting surface, where polarization direction of the incident light is 90° and polarization direction of the scattering light 90° in accordance with an illustrative embodiment. The x-axis is wavelength in nanometers (nm). The y-axis is enhancement factor in AU.
Figure 8:
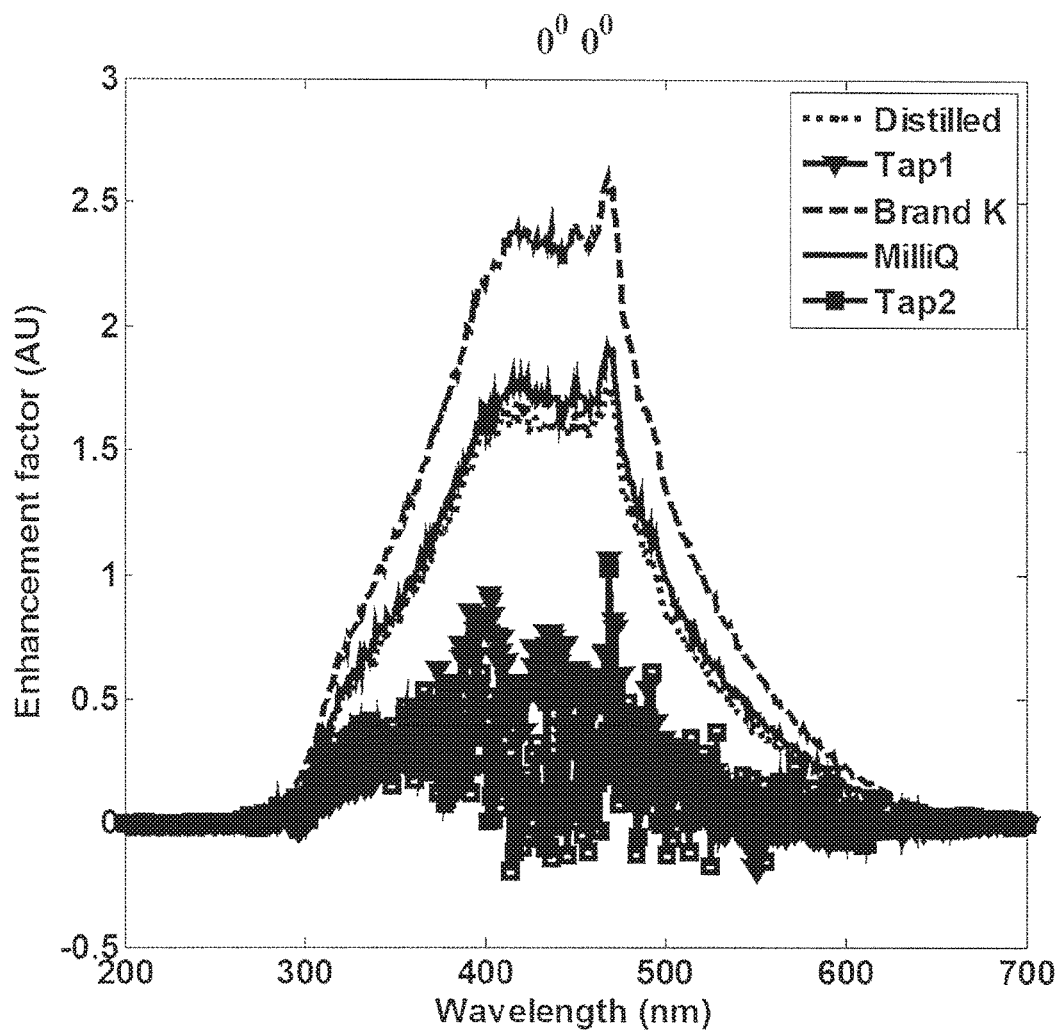
FIG. 8 is a graph illustrating normalized difference RLS spectra of five different water samples irradiated with polarized light in the presence of a reflecting surface, where polarization direction of the incident light is 0° and polarization direction of the scattering light is 0° in accordance with an illustrative embodiment. The x-axis is wavelength in nanometers (nm). The y-axis is enhancement factor in AU.
Figure 9:
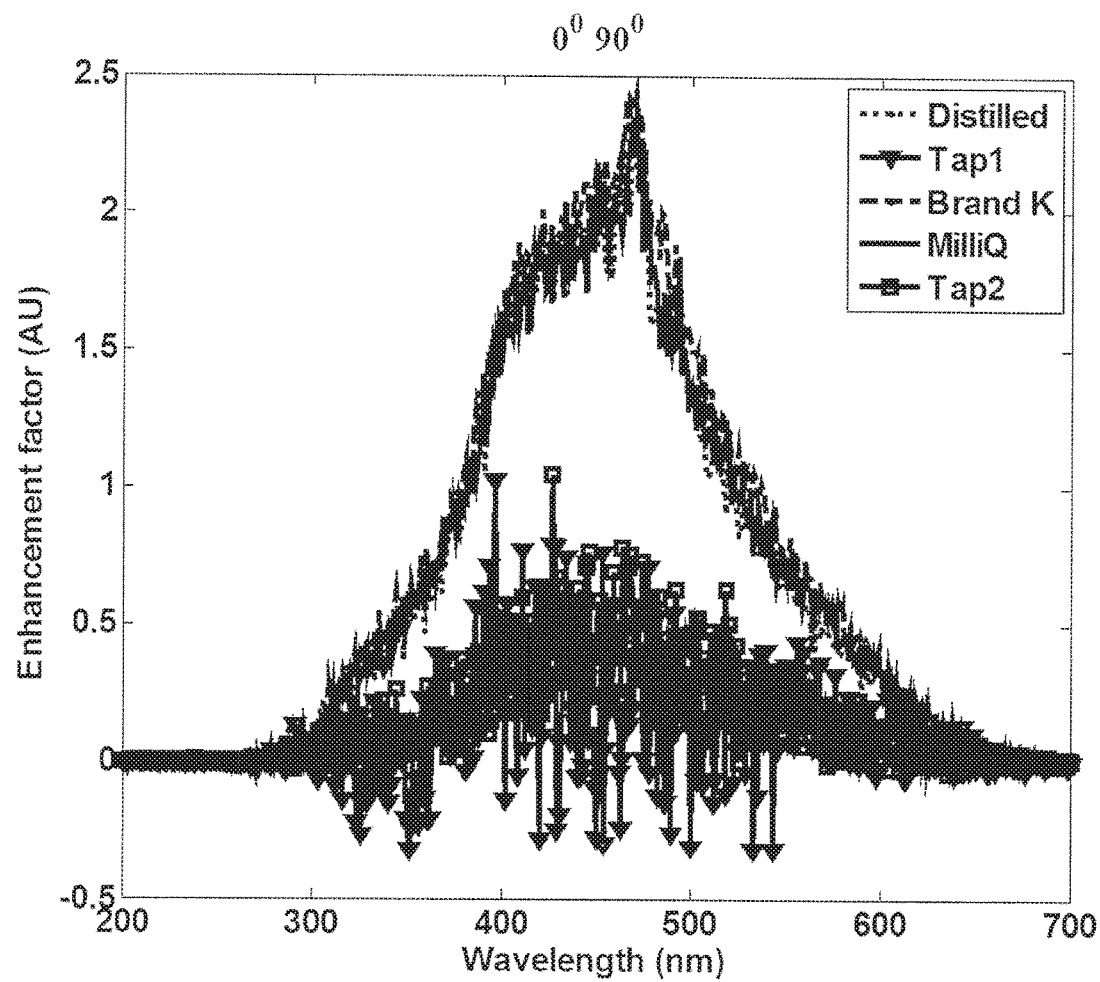
FIG. 9 is a graph illustrating normalized difference RLS spectra of five different water samples irradiated with polarized light in the presence of a reflecting surface, where polarization direction of the incident light is 0° and polarization of the scattering light is 90° in accordance with an illustrative embodiment. The x-axis is wavelength in nanometers (nm). The y-axis is enhancement factor in AU.

The incident/scattering polarization directions were 90°/0° in FIG. 6, 90°/90° in FIG. 7, 0°/0° in FIG. 8, and 0°/90° in FIG. 9. In FIG. 6, intensities of resonance peaks, for example, the 425 nm peak and the 490 nm peak, were about 2.3-2.7 times greater than the corresponding intensities of the resonance peaks in the absence of the reflecting surface. The highest peak in FIG. 6 was about 2.7 times greater in intensity than the corresponding intensity of the resonance peak in FIG. 5. In FIG. 7, intensities of resonance peaks, for example, the 425 nm peak and the 490 nm peak, were 3.0-4.5 times greater than the corresponding intensities of the resonance peaks in FIG. 5. The highest peak in FIG. 7 was about 4.5 times greater in intensity than the corresponding intensities of the resonance peaks in FIG. 5. In FIG. 8, intensities of resonance peaks, for example, the 425 nm peak and the 490 nm peak, were about 1.7-2.5 times greater than the corresponding intensities of the resonance peaks in FIG. 5. The highest peak was about 2.5 times greater in intensity than the corresponding intensities of the resonance peaks in FIG. 5. In FIG. 9, intensities of resonance peaks, for example, the 425 nm peak and the 490 nm peak, were 2.0-2.5 times greater than the corresponding intensities of the resonance peaks in FIG. 5. The highest peak was about 2.5 times greater in intensity than the corresponding intensities of the resonance peaks in FIG. 5.

As such, for milli-Q, distilled, and brand 'K' water, which were substantially free of ions, significant reflecting surface induced enhancements were observed. The unpolarized Rayleigh scattering spectra for scattered light formed in the absence of the reflecting surface showed a highest peak at about 334 nm. The polarized Rayleigh scattering spectra for scattering light formed in the presence of the reflecting surface showed a resonance peak at 425 nm and a resonance peak at 490 nm with intensities 2-5 times or 200% to 500% greater than the intensity of the 334 nm peak in the spectra for scattered light formed in the absence of the reflecting surface, thereby indicating that the water samples are substantially ion free.

Significant reflecting surface induced enhancements were not observed for the two tap waters. The intensity of the resonance peak in the presence of the reflecting surface is not significantly greater than that in the absence of the reflecting surface.

Reflecting surface induced scattering enhancement was only observed for substantially ion free water. The enhancement diminished with increasing ionic concentration, thereby enabling a correlation of ionic impurities and contaminants to the enhancement, which can, in turn, be used to determine the presence of ionic impurities and their concentrations.

Figure 13:
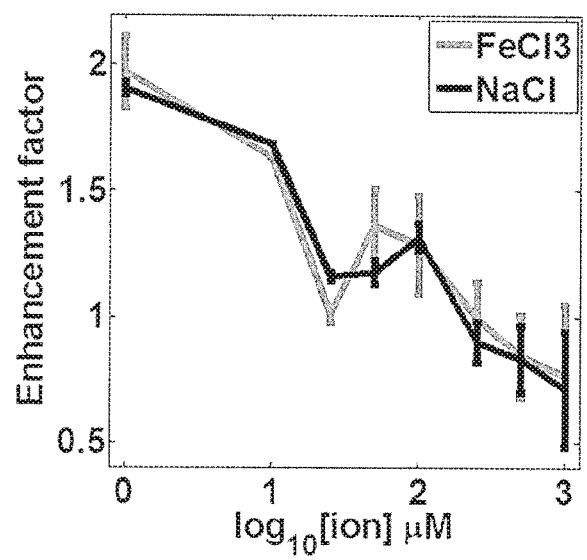
FIG. 13 is a graph illustrating the enhancement factor versus concentration of ionic impurity in a water sample, where the water sample is filtered Milli-Q water from Millipore. The x-axis is the concentration of the ionic purity expressed as $\log_{10}[ion]$ μM. The y-axis is enhancement factor in AU.

FIG. 13 is a graph illustrating the enhancement factor versus concentration of ionic impurities in a water sample. The water sample was filtered Milli-Q water from Millipore. Sodium chloride (NaCl) and iron(III) chloride ($FeCl_3$) were added to the water sample at different concentrations separately. A curve was generated by measuring water samples with the different known ionic levels and plotting them against the respective enhancement factors. The enhancement factor of the tested water sample can be compared to the predetermined values that correspond to known ionic levels of a given impurity in the curve.

Example 2

Rayleigh Light Scattering Spectra of Different Liquid Samples

A white laser was used as a light source and illuminated a 0.2 ml static liquid sample contained in a synthetic quartz container with an incident light. The incident light was provided over a wavelength range of about 300 nm to about 700 nm. The liquid sample scattered light in response to the incident light and emitted the scattered light. The incident light and the scattering light were monochromatized by gratings which have 12 lines per mm and a 500 nm blaze. Polarizers were used to polarize the incident light and the scattered light. The polarizers were Glan Thompson polarizers. A photomultiplier tube (PMT) detector was used to detect the intensity of the scattered light. A polished metal was used as a reflecting surface, which was about 0.1 cm away from the liquid sample at a side opposite to the detector. The reflecting surface of the polished metal was parallel to the propagation direction of the incident light. When the reflecting surface was absent, the incident light was unpolarized. When the reflecting surface was applied, the incident light was polarized. Scattering intensities derived from scattered light formed in the presence and absence of the reflecting surface were detected, and scattering spectra were constructed accordingly.

Ten different liquid samples as listed in Table 1 were tested, namely, dimethyl formamide, dimethyl sulfoxide, acetone, acetonitrile, ethyl acetate, ethyl ether, milli-Q water, n-Hexane, Toluene, and o-Xylene. Matlab codes embodied within the detector were used to construct the scattering spectra. Enhancement factor for each liquid sample was obtained from the constructed spectra.

TABLE 1

Solvent tested and their physical parameters

| Solvents | Polarity Index | Refractive Index | Viscosity (centipoise) | Source and purity |
|---|---|---|---|---|
| Dimethyl formamide | 6.4 | 1.431 | 0.79 | SRL (99%) |
| Dimethyl sulfoxide | 7.2 | 1.479 | 1.99 | Merck (99.9%) |
| Acetone | 5.1 | 1.359 | 0.31 | SRL (99.5%) |
| Acetonitrile | 5.8 | 1.344 | 0.37 | SRL (99.8%) |
| Ethyl acetate | 4.4 | 1.372 | 0.42 | Spectrochem (99.8%) |
| Ethyl ether | 2.8 | 1.352 | 0.22 | SRL (99.5%) |
| Water | 10.2 | 1.333 | 0.89 | Millipore |
| n-Hexane | 0.1 | 1.426 | 0.89 | Merck (96%) |
| Toluene | 2.4 | 1.497 | 0.56 | SRL (99.8%) |
| o-Xylene | 2.5 | 1.505 | 0.76 | SRL (98%) |

Figure 10:
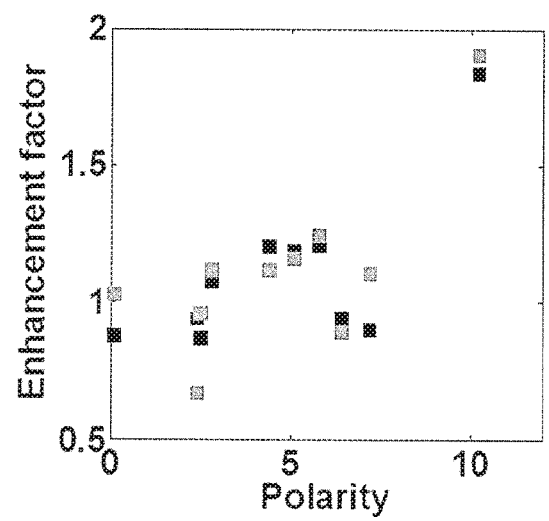
FIG. 10 is a graph illustrating the enhancement factor versus solvent polarity, where polarization direction of the incident light is 0° and polarization of the scattering light is 0° in accordance with an illustrative embodiment. The black and gray points represent duplicate sets. The x-axis is solvent polarity. The y-axis is enhancement factor in AU.
Figure 11:
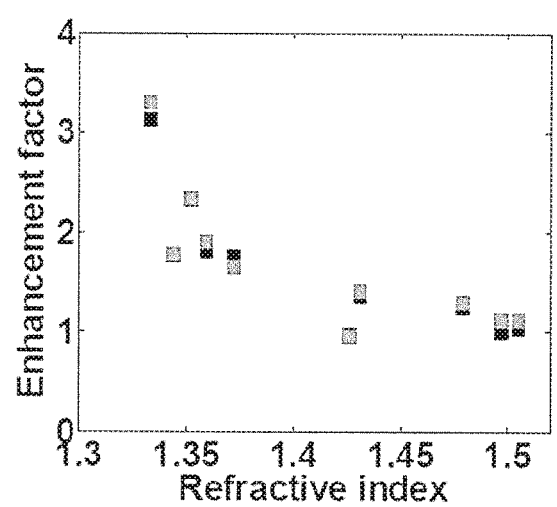
FIG. 11 is a graph illustrating the enhancement factor versus refractive index, where polarization direction of the incident light is 90° and polarization of the scattering light is 90° in accordance with an illustrative embodiment. The black and gray points represent duplicate sets. The x-axis is refractive index. The y-axis is enhancement factor in AU.
Figure 12:
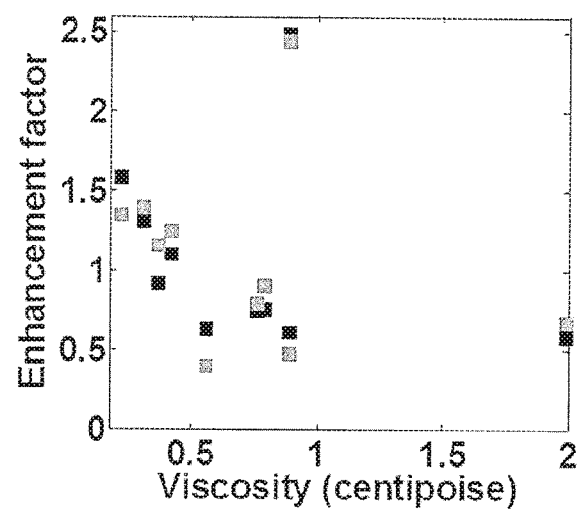
FIG. 12 is a graph illustrating the enhancement factor versus viscosity (centipoise), where polarization direction of the incident light is 0° and polarization of the scattering light is 90° in accordance with an illustrative embodiment. The black and gray points represent duplicate sets. The x-axis is the viscosity. The y-axis is enhancement factor in AU.

FIGS. 10-12 illustrate relationships between the enhancement factor and different physical parameters of the liquid samples. Specifically, FIG. 10 is a graph illustrating the enhancement factor versus solvent polarity. In FIG. 10, polarization direction of the incident light was 0° and polarization of the scattering light was 0°. FIG. 11 is a graph illustrating the enhancement factor versus refractive index. In FIG. 11, polarization direction of the incident light was 90° and polarization of the scattering light was 90°. FIG. 12 is a graph illustrating the enhancement factor versus viscosity (centipoise). In FIG. 12, polarization direction of the incident light was 0° and polarization of the scattering light was 90°.

Example 3

Synchronous Fluorescence Spectra of Different Water Samples

Two water samples were analyzed using the method and system described as follows. The water samples included Milli-Q water and Milli-Q water with dissolved silica. A white light emitting diode was used as a light source for an excitation light to illuminate a 0.5 ml static water sample contained in a transparent synthetic quartz container. The excitation light was monochromatized by a first monochromator having a grating of 2400 lines per mm and a 400 nm blaze. A fluorescence was emitted by the water sample in response to the incident light. The fluorescence emission was monochromatized by a second monochromator having a grating of the same configuration. The excitation light and the emitted fluorescence were polarized by thin film polarizers. The excitation light was provided over a wavelength range of about 300 nm to about 500 nm. The fluorescence intensity of the water sample was determined by a photomultiplier tube (PMT) detector. During detection of the fluorescence intensity, the first monochromator and the second monochromator varied an excitation wavelength and an emission wavelength of light across the 300 nm to 500 nm wavelength range while maintaining a fixed difference between the excitation wavelength and the emission wavelength of 60 nm. A fluorescence spectrum was constructed based on the detected polarized fluorescence intensities using Matlab software embodied within the detector.

Figure 14:
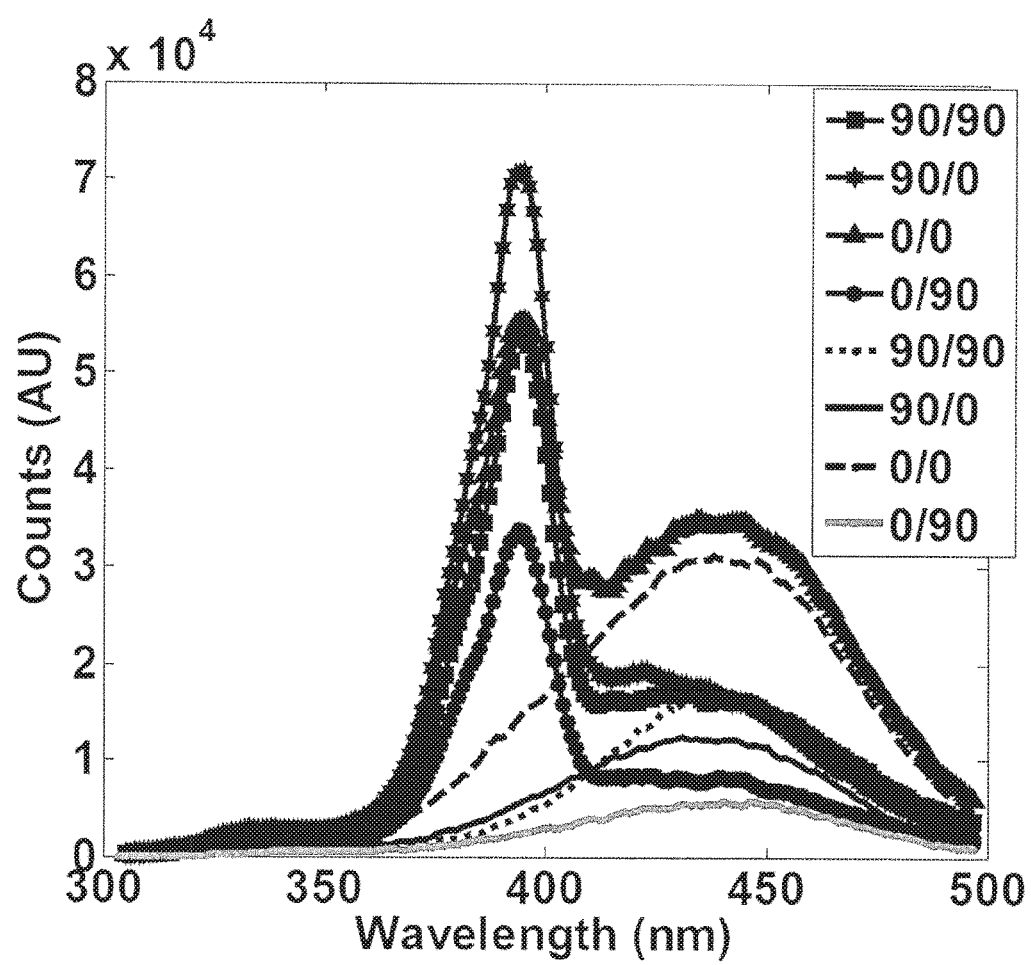
FIG. 14 is a graph illustrating synchronous fluorescence spectra (SFS) of pure milli-Q water and milli-Q water containing 250 PPM soluble silica under four different excitation/emission polarization direction combinations in accordance with an illustrative embodiment. The x-axis is wavelength in nanometers (nm). The y-axis is counts in AU.

FIG. 14 is a graph illustrating synchronous fluorescence spectra (SFS) of pure milli-Q water and milli-Q water containing 250 PPM dissolved silica (ortho-silicic acid, $H_4SiO_4$) under four different combinations of excitation/emission polarization directions, namely, 90°/0°, 90°/90°, 0°/90°, and 0°/0°. Curves with embedded symbols (represent by lines with embedded square, asterisk, triangle, and dot symbols) designate milli-Q water containing 250 PPM dissolved silica. Curves without symbols (represented by dotted, continuous, dashed and grey colored lines) designate pure milli-Q water. A fluorescence peak was observed at about 395 nm for Milli-Q water with dissolved silica. Pure Milli-Q water sample did not show a peak at 395 nm. The pattern and intensity of the peak was sensitive to polarization directions of the excitation light and the emission light. The maximum intensity of the 395 nm peak was seen for the excitation/emission directions combination 90°/0°, while the minimum was found at the combination 0°/90°.

The fluorescence intensity peak and position in the spectrum for the Milli-Q water with dissolved silica were compared to pre-determined relationships of emission peaks and dissolved silica concentration stored in a look-up table in a memory associated with the detector. It was determined that the fluorescence intensity peak and position correspond to soluble silica concentration in the amount of 250 parts-per-million (PPM).

Figure 15:
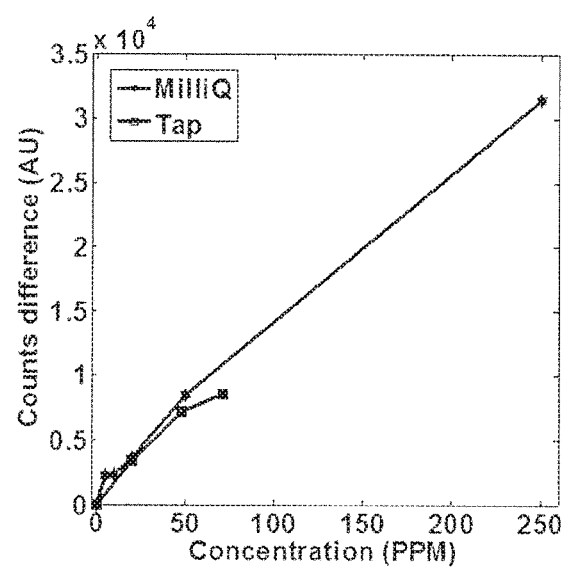
FIG. 15 is a graph illustrating the intensity of the fluorescence peak versus the concentration of dissolved silica in Milli-Q water and tap water, where polarization direction of the excitation light is 90° and polarization direction of the emission light is 0° in accordance with an illustrative embodiment. The x-axis is concentration in ppm. The y-axis is counts difference in AU.

FIG. 15 is a graph illustrating the intensity of the fluorescence peak versus the concentration of dissolved silica in Milli-Q water and a tap water, where the polarization direction of the excitation light is 90° and the polarization direction of the emission lights is 0°. In FIG. 15, the lowest detectable concentration of soluble silica was 5 PPM in milli-Q water and 20 PPM in the tap water. The decreased sensitivity in tap water can be explained by quenching of fluorescence by iron ions, as iron is a strong fluorescence quencher and concentration of iron in tap water is higher than milli-Q water. The sensitivity could be increased if the tap water was pre-treated by iron specific chelating agents.

Figure 16:
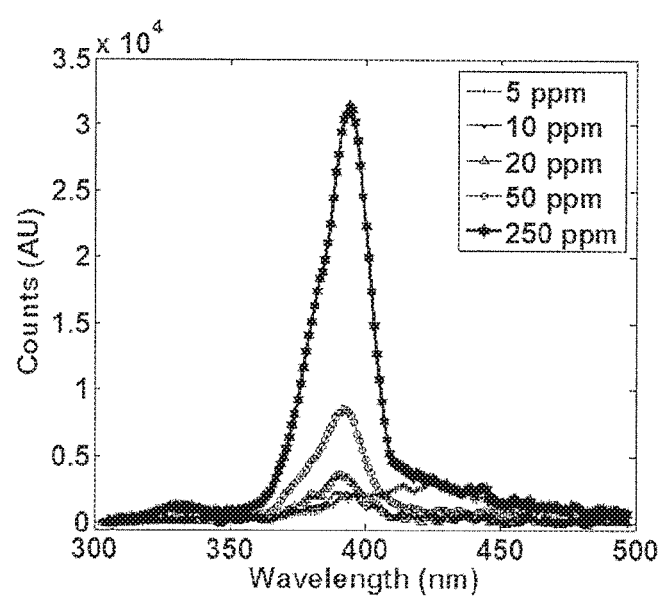
FIG. 16 is a graph illustrating synchronous fluorescence spectra (SFS) of milli-Q water with different concentration of soluble silica, where polarization direction of the excitation light is 90° and polarization direction of the emission light is 0° in accordance with an illustrative embodiment. The x-axis is wavelength in nanometers (nm). The y-axis is counts in AU.
Figure 17:
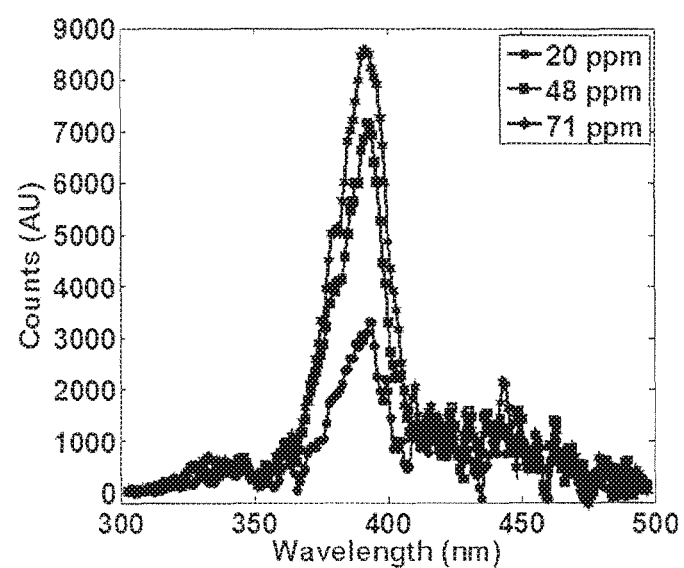
FIG. 17 is a graph illustrating synchronous fluorescence spectra (SFS) of tap water with different concentration of soluble silica, where polarization direction of the excitation light is 90° and polarization direction of the emission light is 0° in accordance with an illustrative embodiment. The x-axis is wavelength in nanometers (nm). The y-axis is counts in AU.

FIG. 16 is a graph illustrating synchronous fluorescence spectra (SFS) of milli-Q water with different concentration of soluble silica. In FIG. 16, the polarization direction of the excitation light was 90° and the polarization direction of the emission light was 0°. The concentration range of soluble silica was from 5 to 250 PPM. FIG. 13 is a graph illustrating synchronous fluorescence spectra (SFS) of tap water with different concentration of soluble silica. In FIG. 17, the polarization direction of the excitation light was 90° and the polarization direction of the emission light was 0°. The concentration range of soluble silica was from 20 to 71 PPM.

Example 4

Detection of Biological Impurities by Using Synchronous Fluorescence Spectra

Biological impurities in a water sample can be detected by measuring synchronous fluorescence spectra. A white laser is used as a light source for an excitation light to illuminate a 0.8 mL flowing water sample that possibly contains biological impurities, such as protein or bacterial impurities. The excitation light is monochromatized by a first monochromator having a grating of 1200 lines per mm and a 500 nm blaze. The fluorescence emission by the water sample in response to the incident light is monochromatized by a second monochromator having a grating of the same configuration. The excitation light and the emitted fluorescence are polarized by Glan-Thompson polarizers. The excitation light is provided over a wavelength range of about 300 nm to about 600 nm. The fluorescence intensity of the water sample is determined by a charge coupled device (COD) based fluorometer.

During detection of the fluorescence intensity, the first monochromator and the second monochromator vary an excitation wavelength and an emission wavelength of light across the 300 nm to 600 nm wavelength range while maintaining a fixed difference between the excitation wavelength and the emission wavelength. For a protein impurity, the fixed difference between the excitation wavelength and the emission wavelength is about 50 nm. For a bacterial impurity, the fixed difference between the excitation wavelength and the emission wavelength is about 100 to 110 nm. The polarization direction of the excitation light and the polarization direction of the emission light is 0°/0°.

A fluorescence spectrum is constructed based on the detected polarized fluorescence intensities using software embodied within the CCD based fluorometer. The fluorescence intensity peak and position in the spectrum are compared to pre-determined relationships of emission peaks and protein or bacterial impurities concentration stored in a look-up table in a memory associated with the COD based fluorometer, to determine concentrations of the impurities.

Example 5

Detection and Differentiation of Multiple Ionic Impurities by Using Rayleigh Scattering Spectra Multiple ionic impurities, for example, Si, Pb, Ca, As, and Mg, in a water source can be detected by measuring Rayleigh scattering spectra. Multiple water samples from the same water source are treated with different ion specific chelators known to those of skill in the art. For example, chelators specific to Pb, Ca, As, and Mg are applied to a first water sample in order to measure Si ions within the first water sample. Chelators specific to Si, Ca, As, and Mg are applied to a second water sample in order to measure Pb ions within the second water sample, and so on.

Rayleigh scattering can be measured on each of the multiple water samples. A white laser is used as a light source and illuminates the first water sample contained in a transparent container with an incident light. The incident light is provided over a wavelength range of about 350 nm to about 550 nm. The incident light and the scattering light are monochromatized by gratings which have 2400 lines per mm and a 450 nm blaze. Polarizers are used to polarize the incident light and the scattering light. The polarizers are thin film polarizers. A photomultiplier tube (PMT) detector is used to detect the intensity of the scattering light. A reflecting surface can be used to reflect light scattered by the water samples in response to the incident light. When the reflecting surface is absent, the incident light is unpolarized. When the reflecting surface is present, the incident light is polarized. The reflecting surface can be parallel to the propagation direction of the incident light. It can be placed at a side of the water sample opposite to the detector. The reflecting surface can be a polished metal surface.

Scattering intensities derived from scattered light formed in the presence and absence of the reflecting surface are detected, and scattering spectra are constructed accordingly. An enhancement factor, which is the ratio of the highest peak in the spectrum formed with the presence of the reflecting surface to the highest peak in the spectrum formed with the absence of the reflecting surface is calculated. The enhancement factor is compared to a pre-determined relationship between the enhancement factor and Si ion concentration to determine the Si ion concentration of the water sample. Similar measurements are conducted on the second water sample and subsequent water samples to determine the concentrations of the additional ionic impurities. Multiple ionic impurities can thus be determined.

Example 6

Detection and Differentiation of Multiple Ionic Impurities by Using Synchronous Fluorescence Spectra Multiple ionic impurities, for example, Si, Pb, Ca, As, and Mg, in a water sample can be detected by measuring synchronous fluorescence spectra. A Xenon lamp is used as a light source for an excitation light to illuminate a 50 μL static water sample containing multiple ionic impurities. The excitation light is monochromatized by a first monochromator having a grating of 2400 lines per mm and a 400 nm blaze. The fluorescence emission by the water sample in response to the incident light is monochromatized by a second monochromator having a grating of the same configuration. The excitation light and the emitted fluorescence are polarized by Glan-Thompson polarizers. The excitation light is provided over a wavelength range of about 300 nm to about 700 nm. The fluorescence intensity of the water sample is determined by a charge coupled device (CCD) based fluorometer.

During detection of the fluorescence intensity, the first monochromator and the second monochromator vary an excitation wavelength and an emission wavelength of light across the 300 nm to 700 nm wavelength range while maintaining a fixed difference between the excitation wavelength and the emission wavelength. For a first ionic impurity, such as Si, the fixed difference between the excitation wavelength and the emission wavelength is a first difference that is pre-determined and used during a first scanning of the water sample. Then for a second ionic impurity, such as Pb, the fixed difference between the excitation wavelength and the emission wavelength is a second difference that is pre-determined and used during a second scanning. The polarization direction of the excitation light and the polarization direction of the emission light is 90°/0°.

Fluorescence spectra are constructed based on the detected polarized fluorescence intensities using Matlab software embodied within the COD based fluorometer. The fluorescence intensity peaks and positions in the spectra are compared to pre-determined relationships of emission peaks and different types of ionic impurities concentrations stored in a look-up table in a memory associated with the COD based fluorometer.

One or more flow diagrams may have been used herein. The use of flow diagrams is not meant to be limiting with respect to the order of operations performed. The herein described subject matter sometimes illustrates different components contained within, or connected with, different other components. It is to be understood that such depicted architectures are merely illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

We claim:

1. A liquid quality assessment system, comprising:
   a light source configured to illuminate a liquid sample;
   a reflecting surface configured to reflect light scattered by the liquid sample;
   a detector configured to detect light intensity,
   wherein the light source is configured to illuminate the liquid sample with a first incident light when the reflecting surface is absent,
   wherein the detector is configured to detect a first light scattered by the liquid sample in response to the first incident light,
   wherein the light source is configured to illuminate the liquid sample with a second incident light when the reflecting surface is present, and
   wherein the detector is configured to detect a second light, wherein the second light is a combination of:
      light scattered by the liquid sample in response to the second incident light; and
      light reflected by the reflecting surface of the light scattered by the liquid sample in response to the second incident light;
   a first monochromator coupled to a multi-spectrum light emitter and configured to monochromatize the first incident light and the second incident light;
   a first polarizer coupled to the multi-spectrum light emitter and configured to polarize the first incident light and the second incident light;
   a second monochromator configured to monochromatize the first light and the second light scattered by the liquid sample; and
   a second polarizer configured to polarize the first light and the second light scattered by the liquid sample,
   wherein the detector:
      calculates an enhancement factor, and
      compares the enhancement factor to a predetermined threshold.

2. The system of claim 1, further comprising a liquid quality assessor coupled to the detector, wherein the liquid quality assessor is configured to provide a liquid quality indicator based on a comparison of the first light and the second light.

3. The system of claim 1, wherein the light source comprises:
the multi-spectrum light emitter configured to provide the first incident light and the second incident light to the liquid sample.

4. The system of claim 1, wherein the first polarizer is integrated into the light source.

5. The system of claim 1, wherein the light sourse is configured to provide the first incident light and the second incident light over a wavelength range of about 350 nm to about 550 nm.

6. The system of claim 1, wherein the first monochromator includes gratings which have 1200 lines per mm and a 300 nm blaze.

7. The system of claim 1, wherein the reflecting surface is parallel to the propagation direction of the second incident light and opposite to the detector.

8. The system of claim 1, further comprising a spectrum constructor configured to construct a first scattering spectrum from the first light that is detected by the detector, and to construct a second scattering spectrum from the second light that is detected by the detector.

9. The system of claim 8, further comprising:
a spectrum analyzer configured to:
identify a quality factor; and
compare the quality factor to a predetermined quality factor threshold.

10. The system of claim 9, wherein a liquid quality indicator indicates that the liquid sample is substantially ion free if the enhancement factor is at least about 200%.

11. A method of assessing liquid quality, comprising:
providing a first incident light to a liquid sample in an absence of a reflecting surface;
passing the first incident light through a first monochromator between a light source and the liquid sample;
detecting a first scattering intensity of a first light scattered by the liquid sample in response to the first incident light in the absence of the reflecting surface at a detector;
passing the first incident light through a second monochromator between the liquid sample and the detector;
providing a second incident light to the liquid sample in a presence of the reflecting surface;
passing the second incident light through the first monochromator between the light source and the liquid sample;
detecting a second scattering intensity of a second light which is a combination of light scattered by the liquid sample in response to the second incident light and light reflected by the reflecting surface of the light scattered by the liquid sample in response to the second incident light;
passing the second incident light through the second monochromator between the liquid sample and the reflecting surface, and the detector; and
assessing the quality of the liquid sample by comparing the second scattering intensity to the first scattering intensity, wherein assessing the quality of the liquid sample includes:
computing an enhancement factor, and
comparing the enhancement factor to a predetermined threshold.

12. The method of claim 11, further comprising:
preparing a first scattering spectrum from the first scattering intensity; and
preparing a second scattering spectrum from the second scattering intensity,
wherein comparing the enhancement factor to the predetermined threshold includes looking up the predetermined threshold from a lookup table.

13. The method of claim 11, wherein the first light and the second light comprise Rayleigh scattering light.

14. The method of claim 11, wherein the first light and the second light comprise Mie scattering light.

15. The method of claim 11, further comprising:
calibrating the detector using liquid samples obtained by adding sodium chloride at different concentrations to Millipore water.

16. The method of claim 11, further comprising:
calibrating the detector by providing an estimation of ionic level using at least one of:
laser Doppler velocimetry, or
portable conductivity meters.

17. The method of claim 11, wherein the method detects at least one of:
biological impurities, biological contaminants, ionic impurities, or ionic contaminants in the liquid sample.

18. The method of claim 11, wherein the method detects nanoparticles contained in the liquid sample.

19. The method of claim 11, further comprising:
prior to providing the first incident light, treating the liquid sample from a liquid source with a first chelator specific to a first ionic impurity, wherein assessing the quality of the liquid sample comprises assessing a concentration of a second ionic impurity in a first liquid sample by comparing the second scattering intensity to the first scattering intensity.

20. The method of claim 19, further comprising:
treating a second liquid sample from the liquid source with a second chelator specific to the second ionic impurity;
providing a third incident light to the second liquid sample in an absence of the reflecting surface;
detecting a third scattering intensity of a third light scattered by the second liquid sample in response to the third incident light in the absence of the reflecting surface;
providing a fourth incident light to the second liquid sample in the presence of the reflecting surface;
detecting a fourth scattering intensity of a fourth light which is a combination of light scattered by the second liquid sample in response to the fourth incident light and light reflected by the reflecting surface of the light scattered by the second liquid sample in response to the fourth incident light; and
assessing the concentration of the first ionic impurity in the second liquid sample by comparing the fourth scattering intensity to the third scattering intensity.

* * * * *

UNITED STATES PATENT AND TRADEMARK OFFICE
CERTIFICATE OF CORRECTION

PATENT NO. : 9,759,668 B2  
APPLICATION NO. : 14/910809  
DATED : September 12, 2017  
INVENTOR(S) : Dasgupta et al.

Page 1 of 1

It is certified that error appears in the above-identified patent and that said Letters Patent is hereby corrected as shown below:

In Column 11, Line 37, delete "fir e," and insert -- firmware, --, therefor.

In Column 19, Line 13, delete "(COD)" and insert -- (CCD) --, therefor.

In Column 19, Line 33, delete "COD" and insert -- CCD --, therefor.

In Column 20, Line 57, delete "COD" and insert -- CCD --, therefor.

In Column 20, Line 61, delete "COD" and insert -- CCD --, therefor.

In Column 23, Line 8, in Claim 5, delete "sourse" and insert -- source --, therefor.

Signed and Sealed this  
Fifth Day of December, 2017

Joseph Matal  
*Performing the Functions and Duties of the*  
*Under Secretary of Commerce for Intellectual Property and*  
*Director of the United States Patent and Trademark Office*